US012605548B2

(12) United States Patent
Zhang et al.

(10) Patent No.: US 12,605,548 B2
(45) Date of Patent: Apr. 21, 2026

(54) CLOSED LOOP CONTROL IN SPINAL CORD STIMULATION

(71) Applicant: Boston Scientific Neuromodulation Corporation, Valencia, CA (US)

(72) Inventors: Tianhe Zhang, Studio City, CA (US); Rosana Esteller, Santa Clarita, CA (US); Andrew Haddock, Los Angeles, CA (US); Michael Moffitt, Solon, OH (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 412 days.

(21) Appl. No.: 17/650,495

(22) Filed: Feb. 9, 2022

(65) Prior Publication Data

US 2022/0266027 A1 Aug. 25, 2022

Related U.S. Application Data

(60) Provisional application No. 63/153,244, filed on Feb. 24, 2021.

(51) Int. Cl.
*A61N 1/36* (2006.01)
*A61N 1/05* (2006.01)

(52) U.S. Cl.
CPC ....... *A61N 1/36139* (2013.01); *A61N 1/0551* (2013.01); *A61N 1/3615* (2013.01);
(Continued)

(58) Field of Classification Search
CPC .............. A61N 1/36139; A61N 1/0551; A61N 1/3615; A61N 1/36171; A61N 1/36175; A61N 1/36178
See application file for complete search history.

(56) References Cited

U.S. PATENT DOCUMENTS 6,181,969 B1    1/2001    Gord
6,516,227 B1    2/2003    Meadows et al.
                (Continued)

FOREIGN PATENT DOCUMENTS

AU    2019216650 A1    9/2019
WO    2017/100866      6/2017
                (Continued)

OTHER PUBLICATIONS

U.S. Appl. No. 63/162,887, filed Mar. 18, 2021, Esteller et al.
                (Continued)

*Primary Examiner* — William J Levicky
*Assistant Examiner* — Rumaisa Rashid Baig
(74) *Attorney, Agent, or Firm* — Lewis & Reese, PLLC

(57) ABSTRACT

Methods and systems for using sensed neural responses for informing aspects of stimulation therapy are disclosed. For example, features of evoked neural responses, such as evoked compound action potentials (ECAPs) can be used for closed-loop feedback control of stimulation parameters. Aspects of the disclosed methods and systems can differentiate between changes in the sensed neural responses that are caused by the environment at stimulating electrodes and changes in the neural responses that are caused by the environment at sensing electrodes. Embodiments determine changes in the morphology of the neural responses, which morphology changes indicate a degree of change in the stimulating environment. Algorithms and systems for assigning and tracking likelihoods for underlying electrode-tissue changes based on sensed neural responses are disclosed. The feedback control modality may be updated based on such likelihoods. Also disclosed are methods and systems for determining which features of evoked neural responses are more sensitive to changes in the stimulating
(Continued)

environment and less sensitive to changes in the sensing environment.

18 Claims, 19 Drawing Sheets

(52) U.S. Cl.
CPC ..... *A61N 1/36171* (2013.01); *A61N 1/36175* (2013.01); *A61N 1/36178* (2013.01)

(56) References Cited

U.S. PATENT DOCUMENTS

| | | | | |
|---|---|---|---|---|
| 6,558,351 | B1 * | 5/2003 | Steil | A61B 5/7242 |
| | | | | 604/522 |
| 6,625,490 | B1 * | 9/2003 | McClure | A61N 1/3704 |
| | | | | 607/9 |
| 6,738,666 | B1 * | 5/2004 | Park | A61N 1/36542 |
| | | | | 607/18 |
| 8,606,362 | B2 * | 12/2013 | He | A61N 1/0551 |
| | | | | 607/46 |
| 8,620,436 | B2 | 12/2013 | Parramon et al. | |
| 9,155,892 | B2 | 10/2015 | Parker et al. | |
| 9,259,574 | B2 | 2/2016 | Aghassian et al. | |
| 9,381,356 | B2 | 7/2016 | Parker et al. | |
| 9,386,934 | B2 | 7/2016 | Parker et al. | |
| 9,409,020 | B2 | 8/2016 | Parker | |
| 9,872,990 | B2 | 1/2018 | Parker et al. | |
| 9,974,455 | B2 | 5/2018 | Parker et al. | |
| 10,096,385 | B1 | 10/2018 | Thibeault et al. | |
| 10,406,368 | B2 | 9/2019 | Hershey et al. | |
| 10,496,797 | B2 | 12/2019 | Monirabbasi et al. | |
| 10,842,989 | B2 | 11/2020 | Brill et al. | |
| 10,926,092 | B2 | 2/2021 | Esteller et al. | |
| 11,129,989 | B2 * | 9/2021 | Dinsmoor | A61N 1/36064 |
| 11,129,991 | B2 * | 9/2021 | Dinsmoor | A61N 1/36175 |
| 11,439,825 | B2 * | 9/2022 | Dinsmoor | A61N 1/36139 |
| 2003/0045910 | A1 * | 3/2003 | Sorensen | A61N 1/36585 |
| | | | | 607/23 |
| 2004/0054382 | A1 * | 3/2004 | Zhu | A61N 1/3712 |
| | | | | 607/27 |
| 2006/0195159 | A1 * | 8/2006 | Bradley | A61N 1/36185 |
| | | | | 607/48 |
| 2007/0038250 | A1 * | 2/2007 | He | A61N 1/0551 |
| | | | | 607/2 |
| 2007/0185409 | A1 * | 8/2007 | Wu | A61B 5/24 |
| | | | | 600/554 |
| 2008/0058872 | A1 * | 3/2008 | Brockway | G16H 40/67 |
| | | | | 607/2 |
| 2010/0010383 | A1 * | 1/2010 | Skelton | A61N 1/36132 |
| | | | | 600/587 |
| 2010/0010584 | A1 * | 1/2010 | Skelton | A61B 5/6846 |
| | | | | 607/62 |
| 2010/0010590 | A1 * | 1/2010 | Skelton | G16H 40/63 |
| | | | | 607/62 |
| 2010/0114224 | A1 * | 5/2010 | Krause | A61N 1/3605 |
| | | | | 607/28 |
| 2010/0280500 | A1 * | 11/2010 | Skelton | A61B 5/7475 |
| | | | | 604/891.1 |
| 2010/0331922 | A1 * | 12/2010 | DiGiore | A61N 1/36128 |
| | | | | 607/62 |
| 2011/0137180 | A1 * | 6/2011 | Johnson | A61N 1/36039 |
| | | | | 600/478 |
| 2012/0092031 | A1 | 4/2012 | Shi et al. | |
| 2012/0095519 | A1 | 4/2012 | Parramon et al. | |
| 2012/0095529 | A1 | 4/2012 | Parramon et al. | |
| 2013/0116748 | A1 * | 5/2013 | Bokil | A61N 1/36182 |
| | | | | 607/59 |
| 2013/0289665 | A1 | 10/2013 | Marnfeldt et al. | |
| 2014/0194772 | A1 | 7/2014 | Single et al. | |
| 2014/0236042 | A1 | 8/2014 | Parker et al. | |
| 2014/0296737 | A1 | 10/2014 | Parker et al. | |
| 2014/0358193 | A1 * | 12/2014 | Lyons | A61N 1/37229 |
| | | | | 607/48 |
| 2015/0080982 | A1 | 3/2015 | Funderburk | |
| 2015/0157861 | A1 | 6/2015 | Aghassian | |
| 2015/0231402 | A1 | 8/2015 | Aghassian | |
| 2015/0282725 | A1 | 10/2015 | Single et al. | |
| 2015/0313487 | A1 | 11/2015 | Single et al. | |
| 2015/0360033 | A1 | 12/2015 | Koubeissi et al. | |
| 2015/0360038 | A1 | 12/2015 | Zottola et al. | |
| 2016/0157769 | A1 * | 6/2016 | Min | G16H 50/50 |
| | | | | 600/547 |
| 2016/0166164 | A1 | 6/2016 | Obradovic et al. | |
| 2016/0228705 | A1 * | 8/2016 | Crowder | A61N 1/36064 |
| 2016/0287126 | A1 | 10/2016 | Parker et al. | |
| 2016/0287182 | A1 | 10/2016 | Single et al. | |
| 2016/0346534 | A1 * | 12/2016 | Isaacson | A61N 1/36185 |
| 2017/0049345 | A1 | 2/2017 | Single et al. | |
| 2017/0071490 | A1 | 3/2017 | Parker et al. | |
| 2017/0113052 | A1 * | 4/2017 | An | A61N 1/36585 |
| 2017/0135624 | A1 | 5/2017 | Parker et al. | |
| 2017/0173332 | A1 * | 6/2017 | Overstreet | A61N 1/0541 |
| 2017/0216587 | A1 | 8/2017 | Parker et al. | |
| 2017/0224991 | A1 * | 8/2017 | Wingeier | A61N 1/0456 |
| 2017/0361089 | A1 * | 12/2017 | Boggs, II | A61N 1/0551 |
| 2017/0361101 | A1 | 12/2017 | Single et al. | |
| 2018/0071520 | A1 | 3/2018 | Weerakoon et al. | |
| 2018/0071527 | A1 | 3/2018 | Feldman et al. | |
| 2018/0078769 | A1 * | 3/2018 | Dinsmoor | A61N 1/0551 |
| 2018/0110987 | A1 | 4/2018 | Parker et al. | |
| 2018/0117335 | A1 | 5/2018 | Parker et al. | |
| 2018/0132747 | A1 | 5/2018 | Parker et al. | |
| 2018/0132760 | A1 | 5/2018 | Parker et al. | |
| 2018/0133459 | A1 | 5/2018 | Parker et al. | |
| 2018/0140831 | A1 | 5/2018 | Feldman et al. | |
| 2018/0228391 | A1 | 8/2018 | Parker et al. | |
| 2018/0228547 | A1 | 8/2018 | Parker et al. | |
| 2018/0256052 | A1 | 9/2018 | Parker et al. | |
| 2018/0310859 | A1 * | 11/2018 | Knabe | A61B 5/4528 |
| 2018/0369606 | A1 * | 12/2018 | Zhang | A61B 5/4836 |
| 2019/0046800 | A1 * | 2/2019 | Doan | A61N 1/37247 |
| 2019/0070418 | A1 | 3/2019 | Hincapie Ordonez et al. | |
| 2019/0083796 | A1 | 3/2019 | Weerakoon et al. | |
| 2019/0099602 | A1 * | 4/2019 | Esteller | A61N 1/37241 |
| 2019/0175915 | A1 | 6/2019 | Brill et al. | |
| 2019/0209844 | A1 * | 7/2019 | Esteller | A61N 1/36071 |
| 2019/0262609 | A1 * | 8/2019 | Brill | A61N 1/36071 |
| 2019/0269919 | A1 | 9/2019 | Brill et al. | |
| 2019/0275331 | A1 | 9/2019 | Zhu | |
| 2019/0290900 | A1 | 9/2019 | Esteller et al. | |
| 2019/0298992 | A1 | 10/2019 | Zhang et al. | |
| 2019/0299006 | A1 | 10/2019 | Marnfeldt | |
| 2019/0329025 | A1 | 10/2019 | Moffitt et al. | |
| 2019/0343283 | A1 * | 11/2019 | Kelley | A47C 1/03211 |
| 2019/0344083 | A1 | 11/2019 | Marnfeldt et al. | |
| 2019/0366094 | A1 | 12/2019 | Esteller et al. | |
| 2020/0001096 | A1 | 1/2020 | Zhang et al. | |
| 2020/0009367 | A1 * | 1/2020 | Huertas Fernandez | |
| | | | | A61N 1/025 |
| 2020/0061380 | A1 | 2/2020 | Zhang et al. | |
| 2020/0147393 | A1 | 5/2020 | Zhang et al. | |
| 2020/0155019 | A1 | 5/2020 | Esteller et al. | |
| 2020/0179698 | A1 * | 6/2020 | Schepis | A61N 1/365 |
| 2020/0305744 | A1 | 10/2020 | Weerakoon et al. | |
| 2020/0305745 | A1 | 10/2020 | Wagenbach et al. | |
| 2021/0016109 | A1 | 1/2021 | Parker et al. | |
| 2021/0023376 | A1 * | 1/2021 | Hareland | A61N 1/3704 |
| 2021/0121700 | A1 * | 4/2021 | Dinsmoor | A61N 1/36139 |
| 2021/0145629 | A1 * | 5/2021 | Ghuge | G16H 40/63 |
| 2021/0236826 | A1 * | 8/2021 | Sheldon | G16H 40/67 |
| 2021/0236829 | A1 | 8/2021 | Zhang et al. | |
| 2021/0252287 | A1 | 8/2021 | Esteller et al. | |
| 2021/0252289 | A1 | 8/2021 | Esteller | |
| 2021/0379383 | A1 * | 12/2021 | Single | A61N 1/16 |
| 2021/0387004 | A1 * | 12/2021 | Single | A61N 1/36125 |
| 2022/0040485 | A1 * | 2/2022 | Li | A61B 5/40 |
| 2022/0143403 | A1 * | 5/2022 | Offutt | A61N 1/36007 |
| 2022/0233866 | A1 * | 7/2022 | Gururaj | A61N 1/36125 |

(56)                    References Cited

U.S. PATENT DOCUMENTS

| | | | | |
|---|---|---|---|---|
| 2022/0339447 | A1* | 10/2022 | Haddock | A61N 1/3702 |
| 2022/0355112 | A1* | 11/2022 | Weiss | A61N 1/36139 |

FOREIGN PATENT DOCUMENTS

| | | |
|---|---|---|
| WO | 2017/173493 | 10/2017 |
| WO | 2017/219096 | 12/2017 |
| WO | 2019/070406 A1 | 4/2019 |
| WO | 2020/223165 | 11/2020 |
| WO | 2020/251899 | 12/2020 |
| WO | 2021/026151 | 2/2021 |
| WO | 2021/046120 | 3/2021 |
| WO | 2021/080727 | 4/2021 |

OTHER PUBLICATIONS

U.S. Appl. No. 63/165,825, filed Mar. 25, 2021, Esteller et al.
U.S. Appl. No. 63/261,008, filed Sep. 8, 2021, Zhang et al.
U.S. Appl. No. 63/261,584, filed Sep. 24, 2021, Esteller et al.
U.S. Appl. No. 63/266,859, filed Jan. 17, 2022, Annecchino et al.
International Search Report and Written Opinion regarding corresponding PCT Application No. PCT/US2022/070592, mailed May 27, 2022.

* cited by examiner

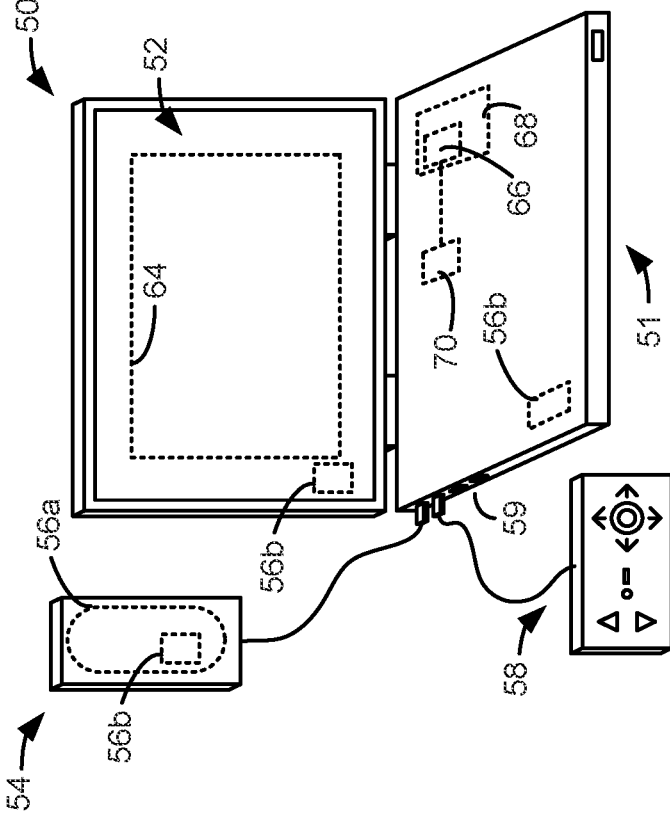
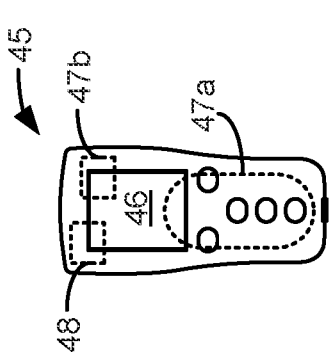
*Figure 4*
*(prior art)*

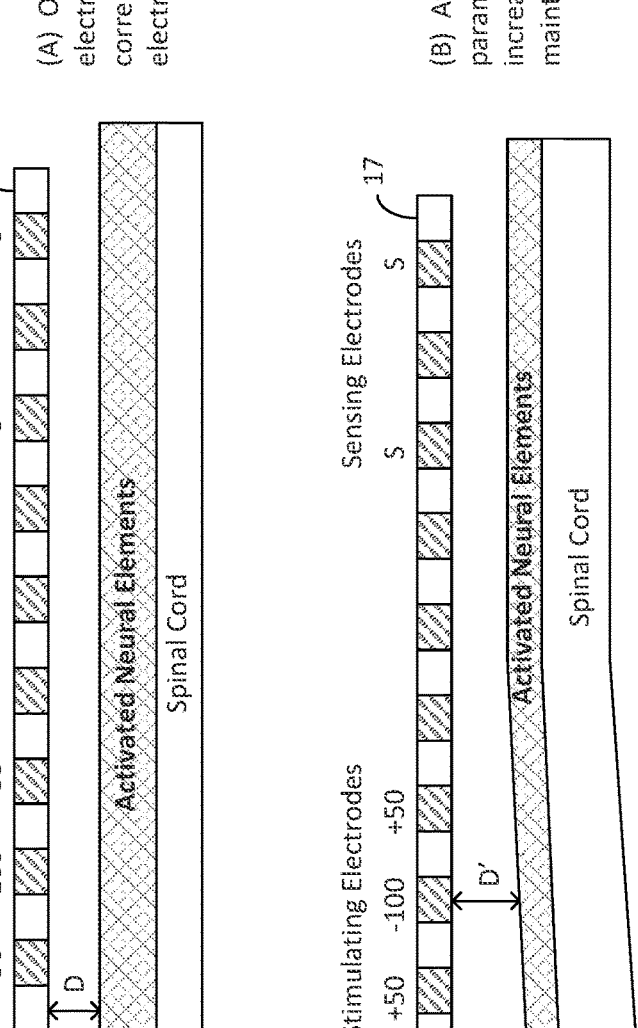

(A) Optimum stimulation at the stimulating electrodes determined in a fitting process is correlated to ECAP measured at the sensing electrodes.

(B) At a greater distance D', the sensed ECAP parameters can be used as feedback to increase the stimulation intensity, thereby maintaining therapy.

(C) At a greater distance D', the sensed ECAP parameters can be used as feedback to increase the stimulation intensity, thereby maintaining therapy.

*Figure 6*

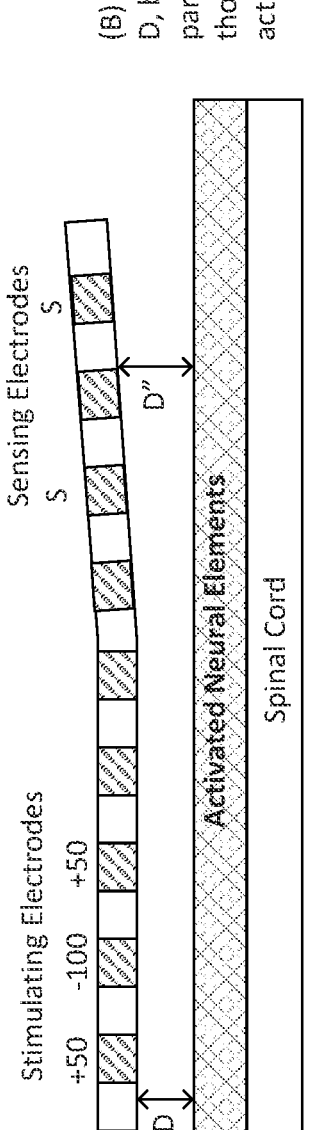

(A) Stimulating electrodes are still at distance D, but sensing electrodes are at D''. ECAP parameters will decrease in magnitude, even though same amount of neural elements are activated by the stimulation.

(B) Stimulating electrodes are still at distance D, but sensing electrodes are at D''. ECAP parameters will decrease in magnitude, even though same amount of neural elements are activated by the stimulation.

*Figure 7*

Figure 10:
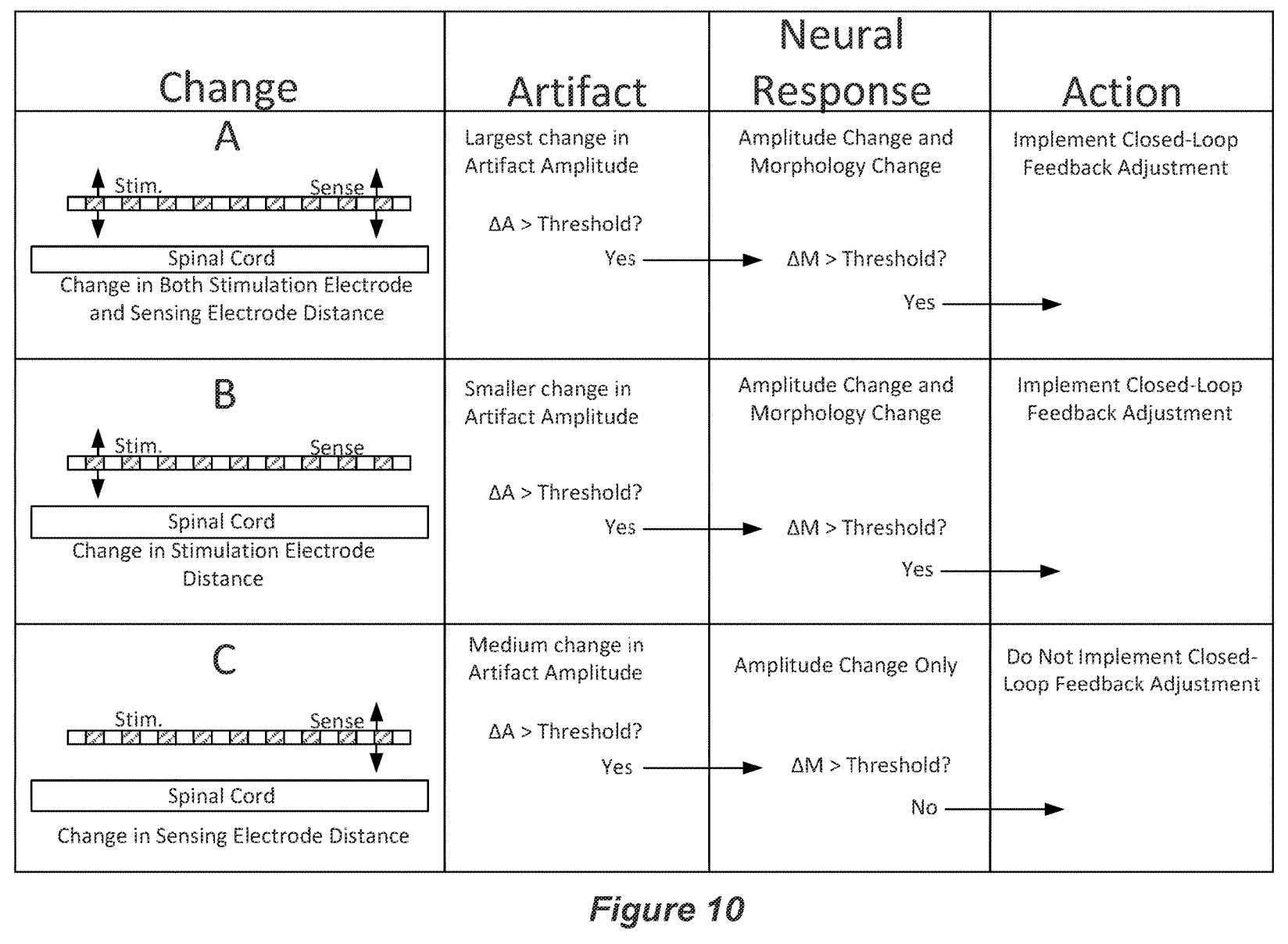

| Change | Artifact | Neural Response | Action |
|---|---|---|---|
| A <br> Stim. — Sense <br> Spinal Cord <br> Change in Both Stimulation Electrode and Sensing Electrode Distance | Largest change in Artifact Amplitude <br><br> ΔA > Threshold? <br> Yes | Amplitude Change and Morphology Change <br><br> ΔM > Threshold? <br> Yes | Implement Closed-Loop Feedback Adjustment |
| B <br> Stim. — Sense <br> Spinal Cord <br> Change in Stimulation Electrode Distance | Smaller change in Artifact Amplitude <br><br> ΔA > Threshold? <br> Yes | Amplitude Change and Morphology Change <br><br> ΔM > Threshold? <br> Yes | Implement Closed-Loop Feedback Adjustment |
| C <br> Stim. — Sense <br> Spinal Cord <br> Change in Sensing Electrode Distance | Medium change in Artifact Amplitude <br><br> ΔA > Threshold? <br> Yes | Amplitude Change Only <br><br> ΔM > Threshold? <br> No | Do Not Implement Closed-Loop Feedback Adjustment |

| Neural Feature (Amplitude) | Event | Sense-dCSF | Stim-dCSF | Likelihood | Therapy Adjustment |
|---|---|---|---|---|---|
| ↑ | 1 | ↓ | ↓ | High | ↓ |
| | 2 | ↓ | ⟷ | Medium | ⟷ |
| | 3 | ↓↓ | ↑ | Very Low | ↑ |
| | 4 | ⟷ | ↓ | Medium | ↓ |
| | 5 | ↑ | ↓↓ | Very Low | ↓↓ |
| ↓ | 6 | ↑ | ↑ | High | ↑ |
| | 7 | ↑ | ⟷ | Medium | ⟷ |
| | 8 | ↑↑ | ↓ | Very Low | ↓ |
| | 9 | ⟷ | ↑ | Medium | ↑ |
| | 10 | ↓ | ↑↑ | Very Low | ↑↑ |
| ⟷ | 11 | ⟷ | ⟷ | High | ⟷ |
| | 12 | ↓ | ↑ | Low | ↑ |
| | 13 | ↑ | ↓ | Low | ↓ |

1402   1404   1406   1408   1410   1412

↑ = Increase

↓ = Decrease

⟷ = No Change

CLOSED LOOP CONTROL IN SPINAL CORD STIMULATION

CROSS-REFERENCE TO RELATED APPLICATIONS

This application is a non-provisional application based on U.S. Provisional Patent Application Ser. No. 63/153,244, filed Feb. 24, 2021, which is incorporated herein by reference, and to which priority is claimed.

FIELD OF THE INVENTION

This application relates to Implantable Medical Devices (IMDs), and more specifically sensing signals in an implantable stimulator device.

INTRODUCTION

Implantable neurostimulator devices are implantable medical devices (IMDs) that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability with any implantable neurostimulator device system.

An SCS system typically includes an Implantable Pulse Generator (IPG) 10 shown in FIG. 1. The IPG 10 includes a biocompatible device case 12 that holds the circuitry and a battery 14 for providing power for the IPG to function. The IPG 10 is coupled to tissue-stimulating electrodes 16 via one or more electrode leads that form an electrode array 17. For example, one or more percutaneous leads 15 can be used having ring-shaped or split-ring electrodes 16 carried on a flexible body 18. In another example, a paddle lead 19 provides electrodes 16 positioned on one of its generally flat surfaces. Lead wires 20 within the leads are coupled to the electrodes 16 and to proximal contacts 21 insertable into lead connectors 22 fixed in a header 23 on the IPG 10, which header can comprise an epoxy for example. Once inserted, the proximal contacts 21 connect to header contacts 24 within the lead connectors 22, which are in turn coupled by feedthrough pins 25 through a case feedthrough 26 to stimulation circuitry 28 within the case 12.

In the illustrated IPG 10, there are thirty-two electrodes (E1-E32), split between four percutaneous leads 15, or contained on a single paddle lead 19, and thus the header 23 may include a 2×2 array of eight-electrode lead connectors 22. However, the type and number of leads, and the number of electrodes, in an IPG is application-specific and therefore can vary. The conductive case 12 can also comprise an electrode (Ec). In a SCS application, the electrode lead(s) are typically implanted in the spinal column proximate to the dura in a patient's spinal cord, preferably spanning left and right of the patient's spinal column. The proximal contacts 21 are tunneled through the patient's tissue to a distant location such as the buttocks where the IPG case 12 is implanted, at which point they are coupled to the lead connectors 22. In other IPG examples designed for implantation directly at a site requiring stimulation, the IPG can be lead-less, having electrodes 16 instead appearing on the body of the IPG 10 for contacting the patient's tissue. The IPG lead(s) can be integrated with and permanently connected to the IPG 10 in other solutions. The goal of SCS therapy is to provide electrical stimulation from the electrodes 16 to alleviate a patient's symptoms, such as chronic back pain.

IPG 10 can include an antenna 27a allowing it to communicate bi-directionally with a number of external devices used to program or monitor the IPG, such as a hand-held patient controller or a clinician's programmer, as described for example in U.S. Patent Application Publication 2019/0175915. Antenna 27a as shown comprises a conductive coil within the case 12, although the coil antenna 27a can also appear in the header 23. When antenna 27a is configured as a coil, communication with external devices preferably occurs using near-field magnetic induction. IPG 10 may also include a Radio-Frequency (RF) antenna 27b. In FIG. 1, RF antenna 27b is shown within the header 23, but it may also be within the case 12. RF antenna 27b may comprise a patch, slot, or wire, and may operate as a monopole or dipole. RF antenna 27b preferably communicates using far-field electromagnetic waves, and may operate in accordance with any number of known RF communication standards, such as Bluetooth, Zigbee, MICS, and the like.

Stimulation in IPG 10 is typically provided by pulses each of which may include a number of phases such as 30a and 30b, as shown in the example of FIG. 2A. Stimulation parameters typically include amplitude (current I, although a voltage amplitude V can also be used); frequency (F); pulse width (PW) of the pulses or of its individual phases; the electrodes 16 selected to provide the stimulation; and the polarity of such selected electrodes, i.e., whether they act as anodes that source current to the tissue or cathodes that sink current from the tissue. These and possibly other stimulation parameters taken together comprise a stimulation program that the stimulation circuitry 28 in the IPG 10 can execute to provide therapeutic stimulation to a patient.

In the example of FIG. 2A, electrode E4 has been selected as an anode (during its first phase 30a), and thus provides pulses which source a positive current of amplitude+I to the tissue. Electrode E5 has been selected as a cathode (again during first phase 30a), and thus provides pulses which sink a corresponding negative current of amplitude −I from the tissue. This is an example of bipolar stimulation, in which only two lead-based electrodes are used to provide stimulation to the tissue (one anode, one cathode). However, more than one electrode may be selected to act as an anode at a given time, and more than one electrode may be selected to act as a cathode at a given time. The case electrode Ec (12) can also be selected as an electrode, or current return, in what is known as monopolar situation.

IPG 10 as mentioned includes stimulation circuitry 28 to form prescribed stimulation at a patient's tissue. FIG. 3 shows an example of stimulation circuitry 28, which includes one or more current source circuits $40_i$ and one or more current sink circuits $42k$. The sources and sinks $40_i$ and $42_i$ can comprise Digital-to-Analog converters (DACs), and may be referred to as PDACs $40_i$ and NDACs $42_i$ in accordance with the Positive (sourced, anodic) and Negative (sunk, cathodic) currents they respectively issue. In the example shown, a NDAC/PDAC $40_i/42_i$ pair is dedicated (hardwired) to a particular electrode node ei 39. Each electrode node ei 39 is connected to an electrode Ei 16 via a DC-blocking capacitor Ci 38, for the reasons explained below. The stimulation circuitry 28 in this example also supports selection of the conductive case 12 as an electrode (Ec 12), which case electrode is typically selected for monopolar stimulation. PDACs 40$_i$ and NDACs 42$_i$ can also comprise voltage sources.

Proper control of the PDACs 40$_i$ and NDACs 42$_i$ allows any of the electrodes 16 to act as anodes or cathodes to create a current through a patient's tissue, R, hopefully with good therapeutic effect. In the example shown (FIG. 2A), and during the first phase 30$a$ in which electrodes E4 and E5 are selected as an anode and cathode respectively, PDAC 404 and NDAC 425 are activated and digitally programmed to produce the desired current, I, with the correct timing (e.g., in accordance with the prescribed frequency F and pulse width PWa). During the second phase 30$b$ (PWb), PDAC 405 and NDAC 424 would be activated to reverse the polarity of the current. More than one anode electrode and more than one cathode electrode may be selected at one time, and thus current can flow through the tissue R between two or more of the electrodes 16.

Power for the stimulation circuitry 28 is provided by a compliance voltage VH. As described in further detail in U.S. Patent Application Publication 2013/0289665, the compliance voltage VH can be produced by a compliance voltage generator 29, which can comprise a circuit used to boost the battery 14's voltage (Vbat) to a voltage VH sufficient to drive the prescribed current I through the tissue R. The compliance voltage generator 29 may comprise an inductor-based boost converter as described in the '665 Publication, or can comprise a capacitor-based charge pump. Because the resistance of the tissue is variable, VH may also be variable, and can be as high as 18 Volts in one example.

Other stimulation circuitries 28 can also be used in the IPG 10. In an example not shown, a switching matrix can intervene between the one or more PDACs 40$_i$ and the electrode nodes ei 39, and between the one or more NDACs 42$_i$ and the electrode nodes. Switching matrices allow one or more of the PDACs or one or more of the NDACs to be connected to one or more anode or cathode electrode nodes at a given time. Various examples of stimulation circuitries can be found in U.S. Pat. Nos. 6,181,969, 8,606,362, 8,620, 436, and U.S. Patent Application Publications 2018/ 0071520 and 2019/0083796. Much of the stimulation circuitry 28 of FIG. 3, including the PDACs 40$_i$ and NDACs 42$_i$, the switch matrices (if present), and the electrode nodes ei 39 can be integrated on one or more Application Specific Integrated Circuits (ASICs), as described in U.S. Patent Application Publications 2012/0095529, 2012/0092031, and 2012/0095519, which are incorporated by reference. As explained in these references, ASIC(s) may also contain other circuitry useful in the IPG 10, such as telemetry circuitry (for interfacing off chip with telemetry antennas 27$a$ and/or 27$b$), the compliance voltage generator 29, various measurement circuits, etc.

Also shown in FIG. 3 are DC-blocking capacitors Ci 38 placed in series in the electrode current paths between each of the electrode nodes ei 39 and the electrodes Ei 16 (including the case electrode Ec 12). The DC-blocking capacitors 38 act as a safety measure to prevent DC current injection into the patient, as could occur for example if there is a circuit fault in the stimulation circuitry 28. The DC-blocking capacitors 38 are typically provided off-chip (off of the ASIC(s)), and instead may be provided in or on a circuit board in the IPG 10 used to integrate its various components, as explained in U.S. Patent Application Publication 2015/ 0157861.

Although not shown, circuitry in the IPG 10 including the stimulation circuitry 28 can also be included in an External Trial Stimulator (ETS) device which is used to mimic operation of the IPG during a trial period and prior to the IPG 10's implantation. An ETS device is typically used after the electrode array 17 has been implanted in the patient. The proximal ends of the leads in the electrode array 17 pass through an incision in the patient and are connected to the externally-worn ETS, thus allowing the ETS to provide stimulation to the patient during the trial period. Further details concerning an ETS device are described in U.S. Pat. No. 9,259,574 and U.S. Patent Application Publication 2019/0175915.

Referring again to FIG. 2A, the stimulation pulses as shown are biphasic, with each pulse at each electrode comprising a first phase 30$a$ followed thereafter by a second phase 30$b$ of opposite polarity. Biphasic pulses are useful to actively recover any charge that might be stored on capacitive elements in the electrode current paths, such as the DC-blocking capacitors 38, the electrode/tissue interface, or within the tissue itself. To recover all charge by the end of the second pulse phase 30$b$ of each pulse (Vc4=Vc5=0V), the first and second phases 30$a$ and 30$b$ are preferably charged balanced at each electrode, with the phases comprising an equal amount of charge but of the opposite polarity. In the example shown, such charge balancing is achieved by using the same pulse width (PWa=PWb) and the same amplitude (|+I|=|−I|) for each of the pulse phases 30$a$ and 30$b$. However, the pulse phases 30$a$ and 30$b$ may also be charged balance if the product of the amplitude and pulse widths of the two phases 30$a$ and 30$b$ are equal, as is known.

FIG. 3 shows that stimulation circuitry 28 can include passive recovery switches 41$k$, which are described further in U.S. Patent Application Publications 2018/0071527 and 2018/0140831. Passive recovery switches 41$_i$ may be attached to each of the electrode nodes 39, and are used to passively recover any charge remaining on the DC-blocking capacitors Ci 38 after issuance of the second pulse phase 30$b$—i.e., to recover charge without actively driving a current using the DAC circuitry. Passive charge recovery can be prudent, because non-idealities in the stimulation circuitry 28 may lead to pulse phases 30$a$ and 30$b$ that are not perfectly charge balanced. Passive charge recovery typically occurs during at least a portion 30$c$ (FIG. 2A) of the quiet periods between the pulses by closing passive recovery switches 41$k$. As shown in FIG. 3, the other end of the switches 41$_i$ not coupled to the electrode nodes 39 are connected to a common reference voltage, which in this example comprises the voltage of the battery 14, Vbat, although another reference voltage could be used. As explained in the above-cited references, passive charge recovery tends to equilibrate the charge on the DC-blocking capacitors 38 and other capacitive elements by placing the capacitors in parallel between the reference voltage (Vbat) and the patient's tissue. Note that passive charge recovery is illustrated as small exponentially-decaying curves during 30$c$ in FIG. 2A, which may be positive or negative depending on whether pulse phase 30$a$ or 30$b$ has a predominance of charge at a given electrode.

FIG. 4 shows various external devices that can wirelessly communicate data with the IPG 10 and/or the ETS 80, including a patient, hand-held external controller 45, and a clinician programmer 50. Both of devices 45 and 50 can be used to wirelessly send a stimulation program to the IPG 10 or ETS 80—that is, to program their stimulation circuitries 28 and 44 to produce pulses with a desired shape and timing described earlier. Both devices 45 and 50 may also be used to adjust one or more stimulation parameters of a stimulation program that the IPG 10 or ETS 80 is currently executing. Devices 45 and 50 may also receive information from the IPG 10 or ETS 80, such as various status information, etc.

External controller 45 can be as described in U.S. Patent Application Publication 2015/0080982 for example, and may comprise either a dedicated controller configured to work with the IPG 10. External controller 45 may also comprise a general purpose mobile electronics device such as a mobile phone which has been programmed with a Medical Device Application (MDA) allowing it to work as a wireless controller for the IPG 10 or ETS 80, as described in U.S. Patent Application Publication 2015/0231402. External controller 45 includes a user interface, including means for entering commands (e.g., buttons or icons) and a display 46. The external controller 45's user interface enables a patient to adjust stimulation parameters, although it may have limited functionality when compared to the more-powerful clinician programmer 50, described shortly.

The external controller 45 can have one or more antennas capable of communicating with the IPG 10 and ETS 80. For example, the external controller 45 can have a near-field magnetic-induction coil antenna 47a capable of wirelessly communicating with the coil antenna 27a or 42a in the IPG 10 or ETS 80. The external controller 45 can also have a far-field RF antenna 47b capable of wirelessly communicating with the RF antenna 27b or 42b in the IPG 10 or ETS 80.

The external controller 45 can also have control circuitry 48 such as a microprocessor, microcomputer, an FPGA, other digital logic structures, etc., which is capable of executing instructions in an electronic device. Control circuitry 48 can for example receive patient adjustments to stimulation parameters, and create a stimulation program to be wirelessly transmitted to the IPG 10 or ETS 80.

Clinician programmer 50 is described further in U.S. Patent Application Publication 2015/0360038, and is only briefly explained here. The clinician programmer 50 can comprise a computing device 51, such as a desktop, laptop, or notebook computer, a tablet, a mobile smart phone, a Personal Data Assistant (PDA)-type mobile computing device, etc. In FIG. 4, computing device 51 is shown as a laptop computer that includes typical computer user interface means such as a screen 52, a mouse, a keyboard, speakers, a stylus, a printer, etc., not all of which are shown for convenience. Also shown in FIG. 4 are accessory devices for the clinician programmer 50 that are usually specific to its operation as a stimulation controller, such as a communication "wand" 54, and a joystick 58, which are coupleable to suitable ports on the computing device 51, such as USB ports 59 for example.

The antenna used in the clinician programmer 50 to communicate with the IPG 10 or ETS 80 can depend on the type of antennas included in those devices. If the patient's IPG 10 or ETS 80 includes a coil antenna 27a or 82a, wand 54 can likewise include a coil antenna 56a to establish near-filed magnetic-induction communications at small distances. In this instance, the wand 54 may be affixed in close proximity to the patient, such as by placing the wand 54 in a belt or holster wearable by the patient and proximate to the patient's IPG 10 or ETS 80. If the IPG 10 or ETS 80 includes an RF antenna 27b or 82b, the wand 54, the computing device 51, or both, can likewise include an RF antenna 56b to establish communication with the IPG 10 or ETS 80 at larger distances. (Wand 54 may not be necessary in this circumstance). The clinician programmer 50 can also establish communication with other devices and networks, such as the Internet, either wirelessly or via a wired link provided at an Ethernet or network port.

To program stimulation programs or parameters for the IPG 10 or ETS 80, the clinician interfaces with a clinician programmer graphical user interface (GUI) 64 provided on the display 52 of the computing device 51. As one skilled in the art understands, the GUI 64 can be rendered by execution of clinician programmer software 66 on the computing device 51, which software may be stored in the device's non-volatile memory 68. One skilled in the art will additionally recognize that execution of the clinician programmer software 66 in the computing device 51 can be facilitated by controller circuitry 70 such as a microprocessor, microcomputer, an FPGA, other digital logic structures, etc., which is capable of executing programs in a computing device. In one example, controller circuitry 70 can include any of the i5 Core Processors, manufactured by Intel Corp. Such controller circuitry 70, in addition to executing the clinician programmer software 66 and rendering the GUI 64, can also enable communications via antennas 56a or 56b to communicate stimulation parameters chosen through the GUI 64 to the patient's IPG 10.

While GUI 64 is shown as operating in the clinician programmer 50, the user interface of the external controller 45 may provide similar functionality as the external controller 45 may have similar controller circuitry, software, etc.

SUMMARY

Disclosed herein is a method of providing stimulation to a patient's neural tissue, wherein the patient is implanted with one or more electrode leads comprising a plurality of electrodes, the method comprising: using one or more of the plurality of electrodes as stimulating electrodes to provide stimulation to the patient's neural tissue, using one or more of the plurality of electrodes as sensing electrodes to sense neural responses evoked by the stimulation, determining a first value for a first feature of the sensed neural responses, wherein the first feature is indicative of an amplitude of the sensed neural responses, monitoring for a change in the first value, upon detection of a change in the first value, determining whether to adjust the stimulation, wherein the determining comprises: determining a second value for a second feature of the sensed neural responses, wherein the second feature is indicative of a shape of the sensed neural responses, and using the second value to determine whether to adjust the stimulation, and if it is determined to adjust the stimulation, adjusting the stimulation based on one or more of the first value and the second value. According to some embodiments, the at least one second feature is more sensitive to changes in an environment between the stimulating electrodes and the neural tissue than to changes in an environment between the sensing electrodes and the neural tissue. According to some embodiments, the changes in an environment between the stimulating electrodes and the neural tissue comprise changes in a thickness of cerebro-spinal fluid (dCSF) between the stimulating electrodes and the neural tissue. According to some embodiments, the first feature comprises one or more of an amplitude of any peak of the sensed neural responses, and area under a curve, a curve length, and a difference between amplitudes of any two peaks of the sensed neural responses. According to some embodiments, the second feature comprises one or more of a duration of a portion of the sensed neural responses, a conduction velocity, a latency of a feature of the sensed neural responses, a number of extrema, skew, and kurtosis. According to some embodiments, using the second value to determine whether to adjust the stimulation comprises determining a difference between the second value and a baseline value and adjusting the stimulation only if the difference exceeds a threshold. According to some embodiments, adjusting the stimulation comprises using a feedback control algorithm to adjust the stimulation. According to some embodiments, the feedback control algorithm adjusts the stimulation to maintain the first value with respect to a set point for the first value. According to some embodiments, the feedback control algorithm comprises a Kalman filter. According to some embodiments, the feedback control algorithm comprises a proportional-integral-derivative (PID) control model. According to some embodiments, the feedback algorithm comprises a gain and wherein the gain is adjusted based on the second value. According to some embodiments, adjusting the stimulation comprises adjusting one or more parameters of the stimulation selected from the group consisting of stimulation amplitude, frequency, pulse width, pulse pattern, and center point of stimulation. According to some embodiments, the method further comprises: using one or more of the sensing electrodes to sense a stimulation artifact, monitoring for a change in the stimulation artifact, and upon detection of a change in the stimulation artifact, determining whether to adjust the stimulation using the at least one second feature of the sensed neural responses to determine whether to adjust the stimulation.

Also disclosed herein is a medical device comprising: a plurality of electrode nodes, each electrode node configured to be coupled to an electrode configured to contact a patient's tissue; and control circuitry configured to: use one or more of the plurality of electrodes as stimulating electrodes to provide stimulation to the patient's neural tissue, use one or more of the plurality of electrodes as sensing electrodes to sense neural responses evoked by the stimulation, determine a first value for a first feature of the sensed neural responses, wherein the first feature is indicative of an amplitude of the sensed neural responses, monitor for a change in the first value, upon detection of a change in the first value, determine whether to adjust the stimulation, wherein the determining comprises: determining a second value for a second feature of the sensed neural responses, wherein the second feature is indicative of a shape of the sensed neural responses, and using the second value to determine whether to adjust the stimulation, and if it is determined to adjust the stimulation, adjust the stimulation based on one or more of the first value and the second value. According to some embodiments, the at least one second feature is more sensitive to changes in an environment between the stimulating electrodes and the neural tissue than to changes in an environment between the sensing electrodes and the neural tissue. According to some embodiments, the changes in an environment between the stimulating electrodes and the neural tissue comprise changes in a thickness of cerebrospinal fluid (dCSF) between the stimulating electrodes and the neural tissue. According to some embodiments, the first feature comprises one or more of an amplitude of any peak of the sensed neural responses, and area under a curve, a curve length, and a difference between amplitudes of any two peaks of the sensed neural responses. According to some embodiments, the second feature comprises one or more of a duration of a portion of the sensed neural responses, a conduction velocity, a latency of a feature of the sensed neural responses, a number of extrema, skew, and kurtosis. According to some embodiments, using the second value to determine whether to adjust the stimulation comprises determining a difference between the second value and a baseline value and adjusting the stimulation only if the difference exceeds a threshold. According to some embodiments, adjusting the stimulation comprises using a feedback control algorithm to adjust the stimulation. According to some embodiments, the feedback control algorithm adjusts the stimulation to maintain the first value with respect to a set point for the first value. According to some embodiments, the feedback control algorithm comprises a Kalman filter. According to some embodiments, the feedback control algorithm comprises a proportional-integral-derivative (PID) control model. According to some embodiments, the feedback algorithm comprises a gain and wherein the gain is adjusted based on the second value. According to some embodiments, adjusting the stimulation comprises adjusting one or more parameters of the stimulation selected from the group consisting of stimulation amplitude, frequency, pulse width, pulse pattern, and center point of stimulation. According to some embodiments, the control circuitry is further configured to: use one or more of the sensing electrodes to sense a stimulation artifact, monitor for a change in the stimulation artifact, and upon detection of a change in the stimulation artifact, determine whether to adjust the stimulation using the at least one second feature of the sensed neural responses to determine whether to adjust the stimulation.

Also disclosed herein is a method of providing stimulation to a patient's neural tissue, wherein the patient is implanted with an electrode lead comprising a plurality of electrodes, the method comprising: using one or more of the plurality of electrodes as stimulating electrodes to provide stimulation to the patient's neural tissue, using one or more of the plurality of electrodes as sensing electrodes to sense neural responses evoked by the stimulation, determining at least one feature of the sensed neural responses, upon detection of a change in the at least one feature: determining a likelihood for each of a plurality of events that may have caused the change in the at least one feature, and selecting the event with the highest likelihood, and adjusting the stimulation based on the selected event. According to some embodiments, the plurality of events comprise changes in an environment between the stimulating electrodes and the neural tissue, changes in an environment between the sensing electrodes and the neural tissue, and combinations thereof. According to some embodiments, determining a likelihood for each of the plurality of events comprises using a lookup table that correlates changes in the at least one feature to events and event likelihoods. According to some embodiments, determining a likelihood for each of the plurality of events further comprises adjusting the event likelihoods in the lookup table based on a highest likelihood event determined for a previous measurement. According to some embodiments, the adjusting comprises computing probabilities of an event transition from the highest likelihood event determined for the previous measurement to the events reflected in the lookup table. According to some embodiments, adjusting the stimulation based on the selected event comprises using a control algorithm comprising one or more mathematical models configured to model the sensed neural responses based on modeled environments between the stimulating electrodes and the neural tissue and between the sensing electrodes and the neural tissue. According to some embodiments, the one or more mathematical models comprise one or more of a Kalman filter and a Hidden Markov Model. According to some embodiments, the method further comprises updating the one or more mathematical models based on the determined likelihoods for each of the plurality of events. According to some embodiments, the updating comprises removing events with low likelihoods from the model. According to some embodiments, adjusting the stimulation based on the selected event comprises using a control algorithm comprising a gain and a setpoint, and wherein the method further comprises adjusting one or more of the gain and the setpoint based on the selected event.

Also disclosed herein is a medical device comprising: a plurality of electrode nodes, each electrode node configured to be coupled to an electrode configured to contact a patient's tissue; and control circuitry configured to: use one or more of the plurality of electrodes as stimulating electrodes to provide stimulation to the patient's neural tissue, use one or more of the plurality of electrodes as sensing electrodes to sense neural responses evoked by the stimulation, determine at least one feature of the sensed neural responses, upon detection of a change in the at least one feature: determine a likelihood for each of a plurality of events that could be responsible for the change in the at least one feature, and select the event with the highest likelihood, and adjust the stimulation based on the selected event. According to some embodiments, the plurality of events comprise changes in an environment between the stimulating electrodes and the neural tissue, changes in an environment between the sensing electrodes and the neural tissue, and combinations thereof. According to some embodiments, determining a likelihood for each of the plurality of events comprises using a lookup table that correlates changes in the at least one feature to events and event likelihoods. According to some embodiments, determining a likelihood for each of the plurality of events further comprises adjusting the event likelihoods in the lookup table based on a highest likelihood event determined for a previous measurement. According to some embodiments, the adjusting comprises computing probabilities of an event transition from the highest likelihood event determined for the previous measurement to the events reflected in the lookup table. According to some embodiments, adjusting the stimulation based on the selected event comprises using a control algorithm comprising one or more mathematical models configured to model the sensed neural responses based on modeled environments between the stimulating electrodes and the neural tissue and between the sensing electrodes and the neural tissue. According to some embodiments, the one or more mathematical models comprise one or more of a Kalman filter and a Hidden Markov Model. According to some embodiments, the control circuitry is configured to update the one or more mathematical models based on the determined likelihoods for each of the plurality of events. According to some embodiments, the updating comprises removing events with low likelihoods from the model. According to some embodiments, adjusting the stimulation based on the selected event comprises using a control algorithm comprising a gain and a setpoint, and wherein the method further comprises adjusting one or more of the gain and the setpoint based on the selected event.

Also disclosed herein is a method of determining a best one or more neural response features to use for closed-loop control of stimulation parameters for providing stimulation to a patient's neural tissue, wherein the patient is implanted with an electrode lead comprising a plurality of electrodes, wherein a first plurality of the electrodes are selectable as stimulating electrodes to provide stimulation to the patient's neural tissue and a second plurality of the electrodes are selectable as sensing electrodes to sense a neural response evoked by the stimulation, the method comprising: iteratively selecting a candidate neural response feature from a plurality of neural response features, for each candidate neural response feature: determining a first variability of the neural response feature as a function of a change in an environment between the stimulating electrodes and the patient's neural tissue, determining a second variability of the neural response feature as a function of a change in an environment between the sensing electrodes and the patient's neural tissue, and determining a parameter (J) that is function of the first and second variabilities, and using the parameters (J) for each candidate neural response features to select the best neural response feature for feedback control. According to some embodiments, determining the first variability comprises: (i) using the stimulating electrodes to provide stimulation to the patient's neural tissue while the patient is in a first posture, (ii) sensing a neural response evoked by the stimulation at one or more of the sensing electrodes, (iii) extracting the candidate neural response feature from the sensed neural response, (iv) repeating steps (i)-(iii) for a plurality patient postures, and (v) determining a variability of the candidate neural response feature with respect to the patient postures. According to some embodiments, determining the second variability comprises: (i) using the stimulating electrodes to provide stimulation to the patient's neural tissue while the patient is in a first posture, (ii) sensing a neural response evoked by the stimulation at each of the sensing electrodes, (iii) for each sensing electrode, extracting the candidate neural response feature from the neural response sensed at that electrode, and (v) determining a variability of the candidate neural responses with respect to the sensing electrodes. According to some embodiments, the parameter (J) is a ratio of the second variability to the first variability. According to some embodiments, using the parameters (J) for each candidate neural response features to select the best neural response feature comprises selecting the candidate neural response feature with the lowest value of J.

Also disclosed herein is a device for determining a best one or more neural response features to use for closed-loop control of stimulation parameters for providing stimulation to a patient's neural tissue, wherein the patient is implanted with an electrode lead comprising a plurality of electrodes, wherein a first plurality of the electrodes are selectable as stimulating electrodes to provide stimulation to the patient's neural tissue and a second plurality of the electrodes are selectable as sensing electrodes to sense a neural response evoked by the stimulation, the device comprising: control circuitry configured to: iteratively select a candidate neural response feature from a plurality of neural response features, for each candidate neural response feature: determine a first variability of the neural response feature as a function of a change in an environment between the stimulating electrodes and the patient's neural tissue, determine a second variability of the neural response feature as a function of a change in an environment between the sensing electrodes and the patient's neural tissue, and determine a parameter (J) that is function of the first and second variabilities, and use the parameters (J) for each candidate neural response features to select the best neural response feature for feedback control. According to some embodiments, the device is a clinician's programmer. According to some embodiments, determining the first variability comprises: (i) using the stimulating electrodes to provide stimulation to the patient's neural tissue while the patient is in a first posture, (ii) sensing a neural response evoked by the stimulation at one or more of the sensing electrodes, (iii) extracting the candidate neural response feature from the sensed neural response, (iv) repeating steps (i)-(iii) for a plurality patient postures, and (v) determining a variability of the candidate neural response feature with respect to the patient postures. According to some embodiments, determining the second variability comprises: (i) using the stimulating electrodes to provide stimulation to the patient's neural tissue while the patient is in a first posture, (ii) sensing a neural response evoked by the stimulation at each of the sensing electrodes, (iii) for each sensing electrode, extracting the candidate neural response feature from the neural response sensed at that electrode, and (v) determining a variability of the candidate neural responses with respect to the sensing electrodes. According to some embodiments, the parameter (J) is a ratio of the second variability to the first variability. According to some embodiments, using the parameters (J) for each candidate neural response features to select the best neural response feature comprises selecting the candidate neural response feature with the lowest value of J.

Also disclosed herein is a method of providing stimulation to a patient's neural tissue, wherein the patient is implanted with an electrode lead comprising a plurality of electrodes, the method comprising: using one or more of the plurality of electrodes as stimulating electrodes to provide stimulation to the patient's neural tissue, using one or more of the plurality of electrodes as sensing electrodes to sense one or more neural responses evoked by the stimulation, determining a change in the one or more sensed neural responses, determining an indication of an amount of the change that is attributable to a change in an environment between the one or more stimulating electrodes and the neural tissue and that is not attributable to merely a change in an environment between the one or more sensing electrodes and the neural tissue, and determining how to adjust the stimulation based on the indication. According to some embodiments, the change in an environment between stimulating electrodes and the neural tissue comprises a thickness of cerebrospinal fluid (dCSF) between stimulating electrodes and the neural tissue. According to some embodiments, determining a change in the one or more sensed neural responses comprises determining at least on first feature of the sensed neural responses, wherein the at least one first feature is indicative of an amplitude of the sensed neural responses, and determining a change in the at least one first feature. According to some embodiments, the at least one first feature comprises one or more of an amplitude of any peak of the sensed neural responses and a difference between amplitudes of any two peaks of the sensed neural responses. According to some embodiments, determining an indication of an amount of the change that is attributable to a change in an environment between the one or more stimulating electrodes and the neural tissue and that is not attributable to merely a change in an environment between the one or more sensing electrodes and the neural tissue comprises determining at least one second feature of the sensed neural responses, wherein the at least one second feature is indicative of a shape of the sensed neural responses, and determining a change in the second feature. According to some embodiments, the at least one second feature comprises one or more of a duration of a portion of the sensed neural responses, a conduction velocity, a latency of a feature of the sensed neural responses, a number of extrema, skew, and kurtosis. According to some embodiments, determining an indication of an amount of the change that is attributable to a change in an environment between the one or more stimulating electrodes and the neural tissue and that is not attributable to merely a change in an environment between the one or more sensing electrodes and the neural tissue comprises decomposing the sensed neural responses into a plurality of components and comparing the components to components of a baseline sensed neural response. According to some embodiments, determining an indication of an amount of the change that is attributable to a change in an environment between the one or more stimulating electrodes and the neural tissue and that is not attributable to merely a change in an environment between the one or more sensing electrodes and the neural tissue comprises transforming the sensed neural response from a time domain signal to a frequency domain signal and comparing the frequency domain signal of the sensed neural response to a frequency domain signal of a baseline neural response. According to some embodiments, determining how to adjust the stimulation based on the indication comprises adjusting the stimulation only if the indication exceeds a predetermined threshold. According to some embodiments, determining how to adjust the stimulation based on the indication comprises adjusting the stimulation in an amount proportional to the indication. According to some embodiments, adjusting the stimulation comprises using a feedback control algorithm comprising a gain and a setpoint, wherein one or more of the gain and the setpoint are adjusted based on the indication. Also disclosed herein is a medical device comprising: a plurality of electrode nodes, each electrode node configured to be coupled to an electrode configured to contact a patient's tissue; and control circuitry configured to: use one or more of the plurality of electrodes as stimulating electrodes to provide stimulation to the patient's neural tissue, use one or more of the plurality of electrodes as sensing electrodes to sense neural responses evoked by the stimulation, determine a change in the one or more sensed neural responses, determine an indication of an amount of the change that is attributable to a change in an environment between the one or more stimulating electrodes and the neural tissue and that is not attributable to merely a change in an environment between the one or more sensing electrodes and the neural tissue, and determine how to adjust the stimulation based on the amount of change that is attributable to the change in the environment between the one or more stimulating electrodes and the neural tissue.

The invention may also reside in the form of a programed external device (via its control circuitry) for carrying out the above methods, a programmed IPG or ETS (via its control circuitry) for carrying out the above methods, a system including a programmed external device and IPG or ETS for carrying out the above methods, or as a computer readable media for carrying out the above methods stored in an external device or IPG or ETS.

BRIEF DESCRIPTION OF THE DRAWINGS

FIG. 4 shows external devices able to communicate with the IPG, in accordance with the prior art.

FIG. 6 shows various spinal cord-electrode lead configurations.

FIG. 7 shows various spinal cord-electrode lead configurations.

FIG. 10 shows changes in stimulation artifact and neural response with changes in stimulating and sensing electrodes.

DETAILED DESCRIPTION

Figure 5:
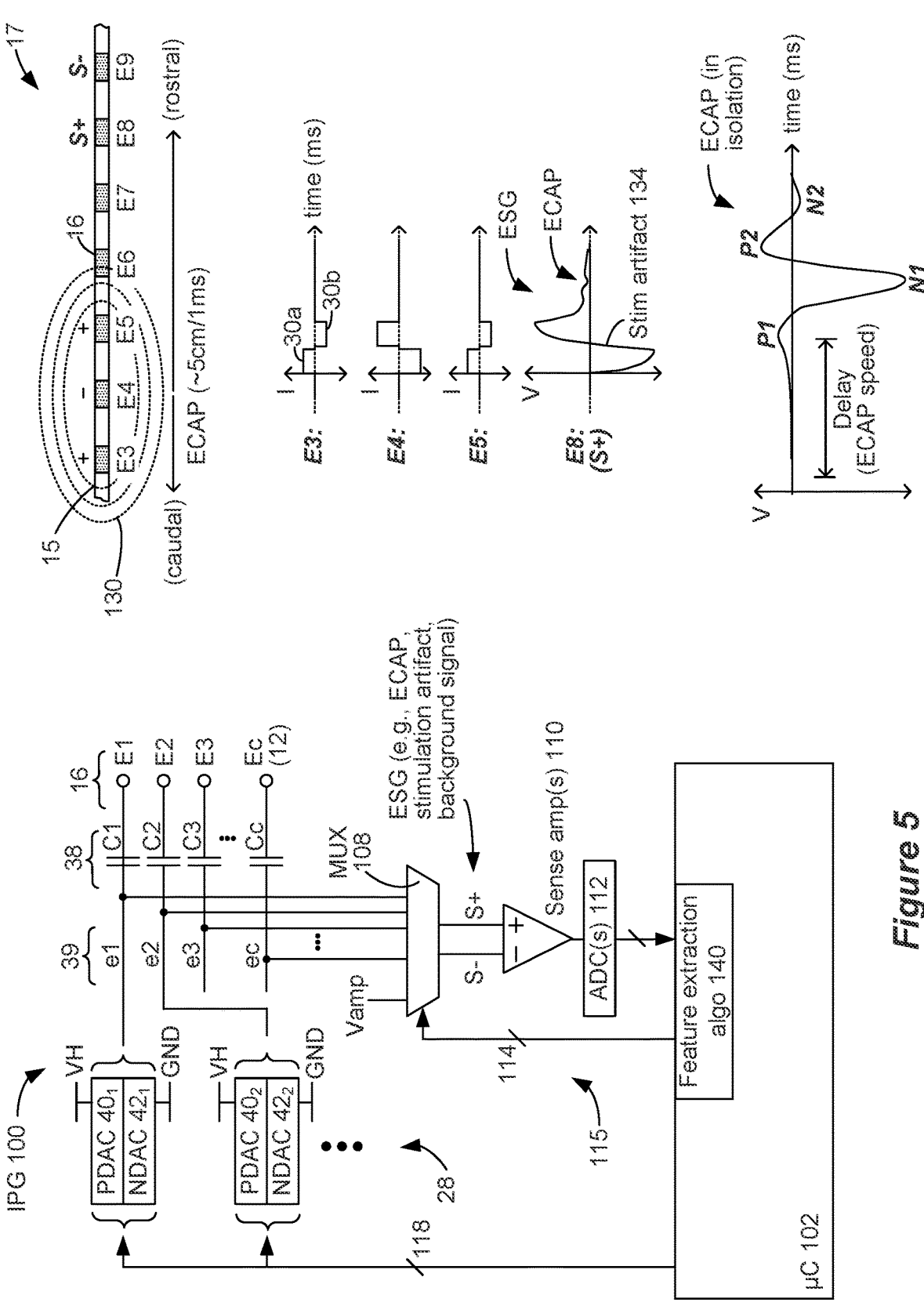
FIG. 5 shows an improved IPG having stimulation capability and the ability to sense an ElectroSpinoGram (ESG) signal which may include Evoked Compound Action Potentials (ECAPs) caused by the simulation.

An increasingly interesting development in pulse generator systems, and in Spinal Cord Stimulator (SCS) pulse generator systems specifically, is the addition of sensing capability to complement the stimulation that such systems provide. FIG. 5 shows an IPG 100 that includes stimulation and sensing functionality. An ETS as described earlier could also include stimulation and sensing capabilities, and the circuitry shown in FIG. 5.

For example, it can be beneficial to sense a neural response in neural tissue that has received stimulation from the IPG 100. One such neural response is an Evoked Compound Action Potential (ECAP). An ECAP comprises a cumulative response provided by neural fibers that are recruited by the stimulation, and essentially comprises the sum of the action potentials of recruited neural elements (ganglia or fibers) when they "fire." An ECAP is shown in isolation in FIG. 5, and comprises a number of peaks that are conventionally labeled with P for positive peaks and N for negative peaks, with P1 comprising a first positive peak, N1 a first negative peak, P2 a second positive peak, N2 a second negative peak, and so on. Note that not all ECAPs will have the exact shape and number of peaks as illustrated in FIG. 5, because an ECAP's shape is a function of the number and types of neural elements that are recruited and that are involved in its conduction. An ECAP is generally a small signal, and may have a peak-to-peak amplitude on the order of hundreds of microvolts or more.

FIG. 5 also shows an electrode array 17 comprising (in this example) a single percutaneous lead 15, and shows use of electrodes E3, E4 and E5 to produce pulses in a tripolar mode of stimulation, with (during the first phase 30*a*) E3 and E5 comprising anodes and E4 a cathode. Other electrode arrangements (e.g., bipoles, etc.) could be used as well. Such stimulation produces an electric field 130 in a volume of the patient's tissue centered around the selected electrodes. Some of the neural fibers within the electric field 130 will be recruited and fire, particularly those proximate to the cathodic electrode E4, forming ECAPs which can travel both rostrally toward the brain and caudally away from the brain. The ECAPs pass through the spinal cord by neural conduction with a speed which is dependent on the neural fibers involved in the conduction. In one example, the ECAP may move at a speed of about 5 cm/1 ms. U.S. Patent Application Publication 2020/0155019 describes a lead that can be useful in the detection of ECAPs.

ECAPs can be sensed at one or more sensing electrodes which can be selected from the electrodes 16 in the electrode array 17. Sensing preferably occurs differentially, with one electrode (e.g., S+, E8) used for sensing and another (e.g., S−, E9) used as a reference. This could also be flipped, with E8 providing the reference (S−) for sensing at electrode E9 (S+). Although not shown, the case electrode Ec (12) can also be used as a sensing reference electrode S−. Sensing reference S− could also comprise a fixed voltage provided by the IPG 100 (e.g., Vamp, discussed below), such as ground, in which case sensing would be said to be single-ended instead of differential.

The waveform appearing at sensing electrode E8 (S+) is shown in FIG. 5, which includes a stimulation artifact 134 as well as an ECAP. The stimulation artifact 134 comprises a voltage that is formed in the tissue as a result of the stimulation, i.e., as a result of the electric field 130 that the stimulation creates in the tissue. As described in U.S. Patent Application Publication 2019/0299006, the voltage in the tissue can vary between ground and the compliance voltage VH used to power the DACs, and so the stimulation artifact 134 can be on the order of Volts, and therefore significantly higher than the magnitude of stimulation-induced ECAPs. Generally speaking, the waveform sensed at the sensing electrode may be referred to as an ElectroSpinoGram (ESG) signal, which comprises the ECAP, the stimulation artifact 134, and other background signals that may be produced by neural tissue even absent stimulation. Realize that the ESG signal as shown at the sensing electrode S+ in FIG. 5 is idealized. The figures in U.S. Patent Application Publication 2022/0323764 show actual recorded ESG traces.

The magnitudes of the stimulation artifact 134 and the ECAP at the sensing electrodes S+ and S− are dependent on many factors, such as the strength of the stimulation, and the distance of sensing electrodes from the stimulation. ECAPs tend to decrease in magnitude at increasing stimulation-to-sensing distances because they disperse in the tissue. Stimulation artifacts 134 also decrease in magnitude at increasing stimulation-to-sensing distances because the electric field 130 is weaker at further distances. Note that the stimulation artifact 134 is also generally larger during the provision of the pulses, although it may still be present even after the pulse (i.e., the last phase 30*b* of the pulse) has ceased, due to the capacitive nature of the tissue or the capacitive nature of the driving circuitry (i.e., the DACs). As a result, the electric field 130 may not dissipate immediately upon cessation of the pulse.

It can be useful to sense in the IPG 100 features of either or both of the ECAPs or stimulation artifact 134 contained within the sensed ESG signal, because such features can be used to useful ends. For example, ECAP features can be used for feedback, such as closed-loop feedback, to adjust the stimulation the IPG 100 provides. See, e.g., U.S. Pat. No.

10,406,368 and U.S. Patent Application Publications 2019/0099602, 2019/0209844, 2019/0070418, 2020/0147393, and 2022/0347479. ECAP assessment can also be used to infer the types of neural elements or fibers that are recruited, which can in turn be used to adjust the stimulation to selectively stimulate such elements. See, e.g., U.S. Patent Application Publication 2019/0275331. Assessments of ECAP features can also be used to determine cardiovascular effects, such as a patient's heart rate. See, e.g., U.S. Patent Application Publication 2019/0290900. To the extent one wishes to assess features of an ECAP that are obscured by a stimulation artifact, U.S. Patent Application Publication 2019/0366094 discloses techniques that can used to extract ECAP features from the ESG signal. As discussed in some of these references, detected ECAPs can also be dependent on a patient's posture or activity, and therefor assessment of ECAP features can be used to infer a patient's posture, which may then in turn be used to adjust the stimulation that the IPG 100 provides.

It can also be useful to detect features of stimulation artifacts 134 in their own right. For example, U.S. Patent Application Publication 2022/0323764 describes that features of stimulation artifacts can be useful to determining patent posture or activity, which again may then in turn be used to adjust the stimulation that the IPG 100 provides.

FIG. 5 shows further details of the circuitry in an IPG 100 that can provide stimulation and sensing an ElectroSpino-Gram (ESG) signal. The IPG 100 includes control circuitry 102, which may comprise a microcontroller, such as Part Number MSP430, manufactured by Texas Instruments, Inc., which is described in data sheets at http://www.ti.com/microcontrollers/msp430-ultra-low-power-mcus/overview.html, which are incorporated herein by reference. Other types of controller circuitry may be used in lieu of a microcontroller as well, such as microprocessors, FPGAs, DSPs, or combinations of these, etc. Control circuitry 102 may also be formed in whole or in part in one or more Application Specific Integrated Circuits (ASICs), such as those described and incorporated earlier.

Figures 1, 2A, 2B:
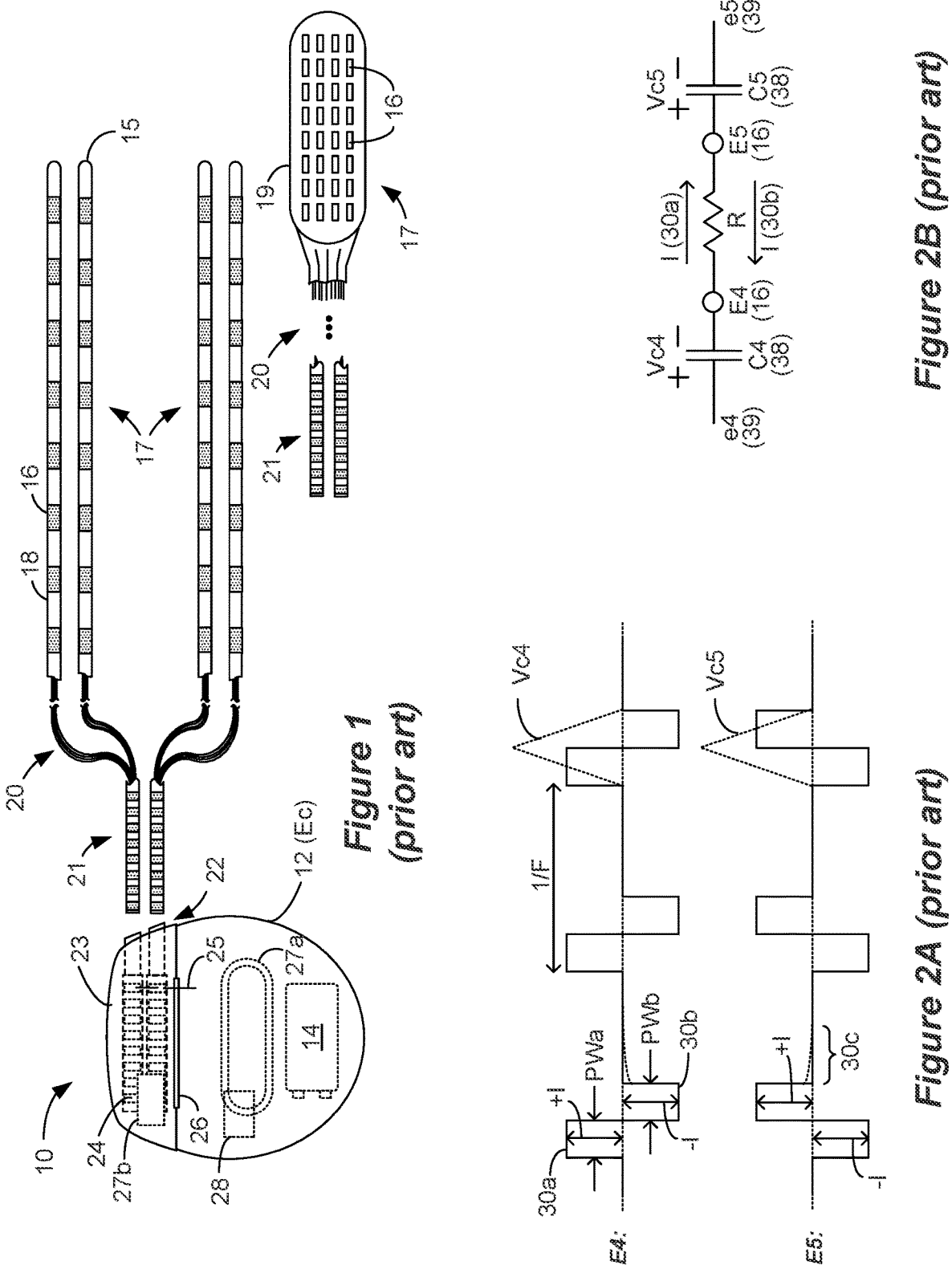
FIG. 1 shows an Implantable Pulse Generator (IPG), in accordance with the prior art.
FIGS. 2A and 2B show an example of stimulation pulses producible by the IPG, in accordance with the prior art.
Figure 3:
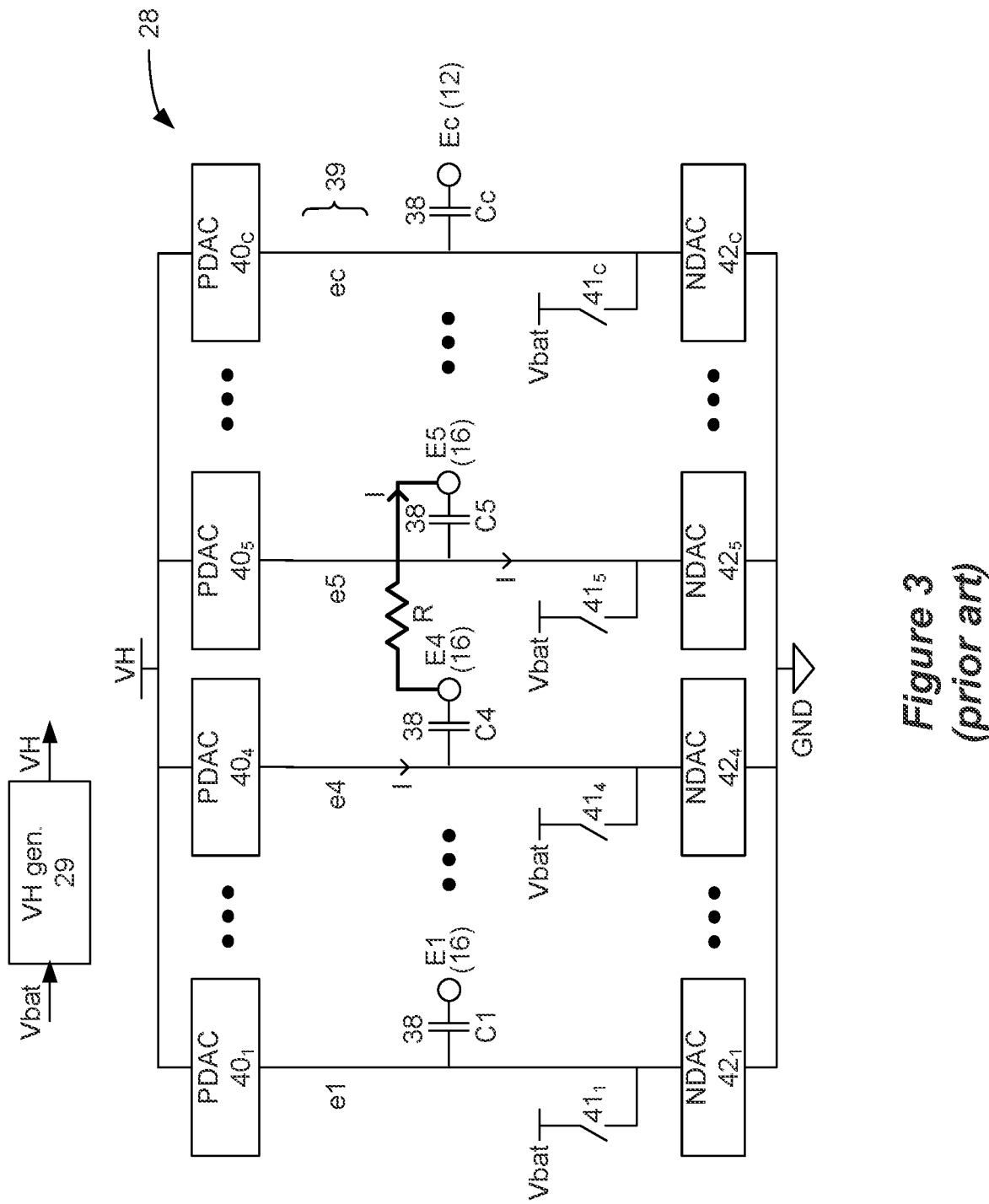
FIG. 3 shows stimulation circuitry useable in the IPG, in accordance with the prior art.

The IPG 100 also includes stimulation circuitry 28 to produce stimulation at the electrodes 16, which may comprise the stimulation circuitry 28 shown earlier (FIG. 3). A bus 118 provides digital control signals from the control circuitry 102 (and possibly from an feature extraction algorithm 140, described below) to one or more PDACs 40$_i$ or NDACs 42$_i$ to produce currents or voltages of prescribed amplitudes (I) for the stimulation pulses, and with the correct timing (PW, F) at selected electrodes. As noted earlier, the DACs can be powered between a compliance voltage VH and ground. As also noted earlier, but not shown in FIG. 4, switch matrices could intervene between the PDACs and the electrode nodes 39, and between the NDACs and the electrode nodes 39, to route their outputs to one or more of the electrodes, including the conductive case electrode 12 (Ec). Control signals for switch matrices, if present, may also be carried by bus 118. Notice that the current paths to the electrodes 16 include the DC-blocking capacitors 38 described earlier, which provide safety by preventing the inadvertent supply of DC current to an electrode and to a patient's tissue. Passive recovery switches 41$_i$ (FIG. 3) could also be present, but are not shown in FIG. 5 for simplicity.

IPG 100 also includes sensing circuitry 115, and one or more of the electrodes 16 can be used to sense signals the ESG signal. In this regard, each electrode node 39 is further coupleable to a sense amp circuit 110. Under control by bus 114, a multiplexer 108 can select one or more electrodes to operate as sensing electrodes (S+, S–) by coupling the electrode(s) to the sense amps circuit 110 at a given time, as explained further below. Although only one multiplexer 108 and sense amp circuit 110 are shown in FIG. 5, there could be more than one. For example, there can be four multiplexer 108/sense amp circuit 110 pairs each operable within one of four timing channels supported by the IPG 100 to provide stimulation. The sensed signals output by the sense amp circuitry are preferably converted to digital signals by one or more Analog-to-Digital converters (ADC(s)) 112, which may sample the output of the sense amp circuit 110 at 50 kHz for example. The ADC(s) 112 may also reside within the control circuitry 102, particularly if the control circuitry 102 has A/D inputs. Multiplexer 108 can also provide a fixed reference voltage, Vamp, to the sense amp circuit 110, as is useful in a single-ended sensing mode (i.e., to set S– to Vamp).

So as not to bypass the safety provided by the DC-blocking capacitors 38, the inputs to the sense amp circuitry 110 are preferably taken from the electrode nodes 39. However, the DC-blocking capacitors 38 will pass AC signal components (while blocking DC components), and thus AC components within the ESG signals being sensed (such as the ECAP and stimulation artifact) will still readily be sensed by the sense amp circuitry 110. In other examples, signals may be sensed directly at the electrodes 16 without passage through intervening capacitors 38.

As noted above, it is preferred to sense an ESG signal differentially, and in this regard, the sense amp circuitry 110 comprises a differential amplifier receiving the sensed signal S+(e.g., E8) at its non-inverting input and the sensing reference S– (e.g., E9) at its inverting input. As one skilled in the art understands, the differential amplifier will subtract S– from S+ at its output, and so will cancel out any common mode voltage from both inputs. This can be useful for example when sensing ECAPs, as it may be useful to subtract the relatively large scale stimulation artifact 134 from the measurement (as much as possible) in this instance. That being said, note that differential sensing will not completely remove the stimulation artifact, because the voltages at the sensing electrodes S+ and S– will not be exactly the same. For one, each will be located at slightly different distances from the stimulation and hence will be at different locations in the electric field 130. Thus, the stimulation artifact 134 can still be sensed even when differential sensing is used. Examples of sense amp circuitry 110, and manner in which such circuitry can be used, can be found in U.S. Patent Application Publications 2019/0299006, 2020/0305744, 2020/0305745, and 2022/0233866.

The digitized ESG signal from the ADC(s) 112—inclusive of any detected ECAPs and stimulation artifacts—is received at a feature extraction algorithm 140 programmed into the IPG's control circuitry 102. The feature extraction algorithm 140 analyzes the digitized sensed signals to determine one or more ECAP features, and one or more stimulation artifact features, as described for example in U.S. Patent Application Publication 2022/0323764. Such features may generally indicate the size and shape of the relevant signals, but may also be indicative of other factors (like ECAP conduction speed). One skilled in the art will understand that the feature extraction algorithm 140 can comprise instructions that can be stored on non-transitory machine-readable media, such as magnetic, optical, or solid-state memories within the IPG 100 (e.g., stored in association with control circuitry 102).

For example, the feature extraction algorithm 140 can determine one or more neural response features (e.g., ECAP features), which may include but are not limited to:

a height of any peak (e.g., N1);

a peak-to-peak height between any two peaks (such as from N1 to P2);

a ratio of peak heights (e.g., N1/P2);

a peak width of any peak (e.g., the full-width half-maximum of N1);

an area or energy under any peak;

a total area or energy comprising the area or energy under positive peaks with the area or energy under negative peaks subtracted or added;

a length of any portion of the curve of the ECAP (e.g., the length of the curve from P1 to N2);

any time defining the duration of at least a portion of the ECAP (e.g., the time from P1 to N2);

a time delay from stimulation to issuance of the ECAP, which is indicative of the neural conduction speed of the ECAP, which can be different in different types of neural tissues;

a conduction speed (i.e., conduction velocity) of the ECAP, which can be determined by sensing the ECAP as it moves past different sensing electrodes;

a rate of variation of any of the previous features, i.e., how such features change over time;

a power (or energy) determined in a specified frequency band (e.g., delta, alpha, beta, gamma, etc.) determined in a specified time window (for example, a time window that overlaps the neural response, the stimulation artifact, etc.);

any mathematical combination or function of these variables;

Such ECAP features may be approximated by the feature extraction algorithm 140. For example, the area under the curve may comprise a sum of the absolute value of the sensed digital samples over a specified time interval. Similarly, curve length may comprise the sum of the absolute value of the difference of consecutive sensed digital samples over a specified time interval. ECAP features may also be determined within particular time intervals, which intervals may be referenced to the start of simulation, or referenced from within the ECAP signal itself (e.g., referenced to peak N1 for example).

In this disclosure, ECAP features, as described above, are also referred to as neural features or neural response features. This is because such ECAP features contain information relating to how various neural elements are excited/ recruited during stimulation, and in addition, how these neural elements spontaneously fired producing spontaneous neural responses as well.

The feature extraction algorithm 140 can also determine one or more stimulation artifact features, which may be similar to the ECAP features just described, but which may also be different to account for the stimulation artifact 134's different shape. Determined stimulation artifact features may include but are not limited to:

a height of any peak;

a peak-to-peak height between any two peaks;

a ratio of peak heights;

an area or energy under any peak;

a total area or energy comprising the area or energy under positive peaks with the area or energy under negative peaks subtracted or added;

a length of any portion of the curve of the stimulation artifact;

any time defining the duration of at least a portion of the stimulation artifact;

a rate of variation of any of the previous features, i.e., how such features change over time;

a power (or energy) determined in a specified frequency band (e.g., delta, alpha, beta, gamma, etc.) determined in a specified time window (for example, a time window that overlaps the neural response, the stimulation artifact, etc.);

any mathematical combination or function of these variables.

Again, such stimulation artifact features may be approximated by the feature extraction algorithm 140, and may be determined with respect to particular time intervals, which intervals may be referenced to the start or end of simulation, or referenced from within the stimulation artifact signal itself (e.g., referenced to a particular peak).

Once the feature extraction algorithm 140 determines one or more of these features, it may then be used to any useful effect in the IPG 100, and specifically may be used to adjust the stimulation that the IPG 100 provides, for example by providing new data to the stimulation circuitry 28 via bus 118. This is explained further in some of the U.S. patent documents cited above. For example, if the distance between the stimulation electrode(s) and the patient's spinal cord changes (for example, because of postural changes, coughing, movement, etc.), the stimulation may be adjusted based on the extracted features to maintain optimum therapeutic stimulation.

This disclosure relates to methods and systems that use neural features for feedback control, such as closed-loop feedback control for adjusting and maintaining stimulation therapy (e.g., SCS therapy). The disclosed methods and systems are particularly useful during the provision of sub-perception therapy. Sub-perception (also known as sub-threshold or paresthesia-free) therapy involves providing stimulation that the patient does not readily perceive. With traditional paresthesia (or supra-threshold) therapy, patients typically perceive sensations, such as tingling sensations, that accompany stimulation. Such sensations are referred to as paresthesia. Sub-perception therapy involves providing stimulation with lower stimulation amplitudes that do not evoke paresthesia and correspond to amplitudes below perception threshold or at sub-threshold stimulation amplitudes. While the disclosed methods and systems are particularly useful for sub-perception therapy, they may also be used to maintain supra-threshold therapy as well.

FIG. 6 illustrates a simplified example of how one or more neural response features (e.g., ECAP features) may be used to provide closed loop feedback for adjusting stimulation. Referring to FIG. 6 A, assume that a patient has been implanted with an electrode lead 17 placed at a distance D near the patient's spinal cord and assume that during a stimulation optimization process (referred to as a fitting procedure) it was determined that stimulation at a certain intensity at the illustrated stimulation electrodes provides optimum therapy for the patient. Assume that the prescribed stimulation activates the illustrated population of neural elements (e.g., a certain amount of fibers) within the patient's spinal cord. Increasing the stimulation intensity beyond the prescribed amount would likely activate more neural elements, which might cause discomfort or other side effects. Decreasing the stimulation intensity would activate fewer neural elements and may not provide adequate relief to the patient. The activated neural elements will elicit a neural response (e.g., an ECAP), which may be sensed at the illustrated sensing electrodes (S). Various features of the sensed neural response can be determined, as described above, and can be used to maintain the optimum therapy, as illustrated in FIGS. 6 B and 6 C.

FIG. 6 B, illustrates a situation where the stimulating environment has changed. Specifically, the stimulating electrodes are further from the patient's spinal cord (new distance D') because the spinal cord has moved. Such a change in the stimulation environment may happen due to the patient changing postures, coughing, laughing, sneezing, etc., or simply because of the patient's heartbeat, breathing, etc. The change in the distance between the stimulating electrodes and the spinal cord causes an increase in the thickness of the cerebrospinal fluid (dCSF) between the stimulating electrodes and the target neural elements, which may impact the effectiveness of the stimulation. Specifically, since the stimulating electrodes are further from the spinal cord, the stimulation may activate fewer neural elements. Since fewer neural elements are activated, the patient's therapy may be degraded. Also, since fewer neural elements are activated, the magnitude of sensed neural response features will decrease. Thus, the sensed neural response intensity (e.g., peak-to-peak amplitude) can be used for closed-loop feedback to increase the stimulation intensity at the new distance D', so as to activate the desired amount of neural elements, thereby maintaining the patent's therapy. Other intensity metrics (such as the area under the curve (AUC), curve length, etc.) may also be used as well.

FIG. 6 C illustrates a similar situation where the stimulation environment has changed, this time due to the stimulating electrodes moving further from the spinal cord (new distance D'). Again, fewer neural elements are activated since the stimulating electrodes have moved further from the spinal cord. The patient's therapy may suffer, and the magnitude of the sensed neural response will be reduced. Thus, the sensed neural response intensity/amplitude can be used for closed loop feedback to increase the stimulation intensity at the new distance D', so as to activate the desired amount of neural elements, thereby maintaining the patent's therapy. It should also be appreciated that similar changes in the stimulation environment can occur wherein the stimulating electrodes move closer to the spinal cord. In that case, the stimulation may activate a greater number of neural elements than desired, which may cause discomfort or other side effects for the patient. Such changes may be reflected as an increase in the sensed magnitude of the neural response and the neural response intensity/amplitude can be used for closed-loop feedback to decrease the stimulation to maintain the appropriate baseline therapy.

The feedback methodology illustrated in FIG. 6 is somewhat naïve because it assumes that changes in the neural response are only due to changes in the stimulating environment and fails to consider that neural response changes may be due to changes in the sensing environment. FIG. 7 illustrates some examples of changes in the sensing environment that may impact sensed neural response features. In FIG. 7A, the stimulating electrodes are still at the original calibrated distance D from the spinal cord. The same amount of neural elements are activated as in FIG. 6 A. However, the distance between the sensing electrodes and the spinal cord is increased because of movement of the spinal cord (new distance D"). Thus, the magnitude of the sensed neural response is decreased because there is more dCSF between the sensing electrodes and the spinal cord, even though the same amount of neural elements are activated by the stimulation. One might naively believe that closed-loop feedback should be implemented to increase the stimulation based on the decrease in the neural response intensity/amplitude. However, increasing the stimulation would recruit more neural elements than desired, which might cause discomfort or other side effects for the patient. This is an example of a "false positive," i.e., an indication that adjustment is needed when it is actually not needed. Likewise, in FIG. 7 B, the distance of the sensing electrodes has increased (new distance D") due to movement of the electrode lead, even though the stimulating electrodes are still at the original distance D from the spinal cord. Thus, the sensed neural response intensity/amplitude will decrease, but increasing stimulation in this situation would recruit a greater than desired amount of neural elements.

The situations illustrated in FIGS. 7 A and 7 B illustrate problems with assuming that changes in sensed neural response intensity (and features derived based only on the sensed neural response intensity) all originate from changes to the stimulation environment and therefore need to be corrected using closed-loop feedback to adjust the stimulation parameters. The goal is to maintain stimulation of the correct neural fibers to maintain the patient's therapy. If the stimulating environment changes, then stimulation may need to be adjusted. However, if the sensing environment changes, then stimulation may not need to be adjusted, even though a change in the neural response intensity is observed. An example, is when the stimulating electrodes' distance does not change, but the sensing electrodes' distance increases (as shown in FIGS. 7 A and 7 B). That is an example of a "false positive," i.e., an indication that adjustment is needed when it is actually not needed. Likewise, "false negatives" can occur, such as when the stimulating electrodes get closer to the spinal cord, but the sensing electrodes get further away. In that case, the sensed neural response intensity may stay relatively constant, even though the stimulation is recruiting too many neural fibers. Other examples of false positives and false negatives will be apparent. Adjusting stimulation in response to false positives or false negatives may result in either lowering stimulation to a point such that therapy is no longer effective or increasing stimulation to point that causes discomfort for the patient.

The inventors have realized that relying on sensed neural response intensity (i.e., neural response amplitude features, AUC, curve length, etc.) alone are not ideal for closed-loop adjustment of stimulation, because doing so assumes that all changes to these features are due to the stimulation environment. Aspects of this disclosure relate to methods and systems for closed-loop adjustment of stimulation parameters based on neural response measurements that are able to discern between changes in the stimulation environment (when closed-loop adjustment is warranted) and changes in the sensing environment (when closed-loop adjustment may not be warranted). As used herein, changes in the stimulation environment may be expressed in terms of stim-dCSF, meaning the width of dCSF between the stimulating electrode(s) and the spinal cord. An increase in stim-dCSF means that the stimulating electrode-spinal cord distance has increased; a decrease in stim-dCSF means that the stimulating electrode-spinal cord distance has decreased. Likewise, changes in the sensing environment may be expressed in terms of sense-dCSF. An increase in sense-dCSF means that the stimulating electrode-spinal cord distance has increased; a decrease in sense-dCSF means that the stimulating electrode-spinal cord distance has decreased.

Figure 8:
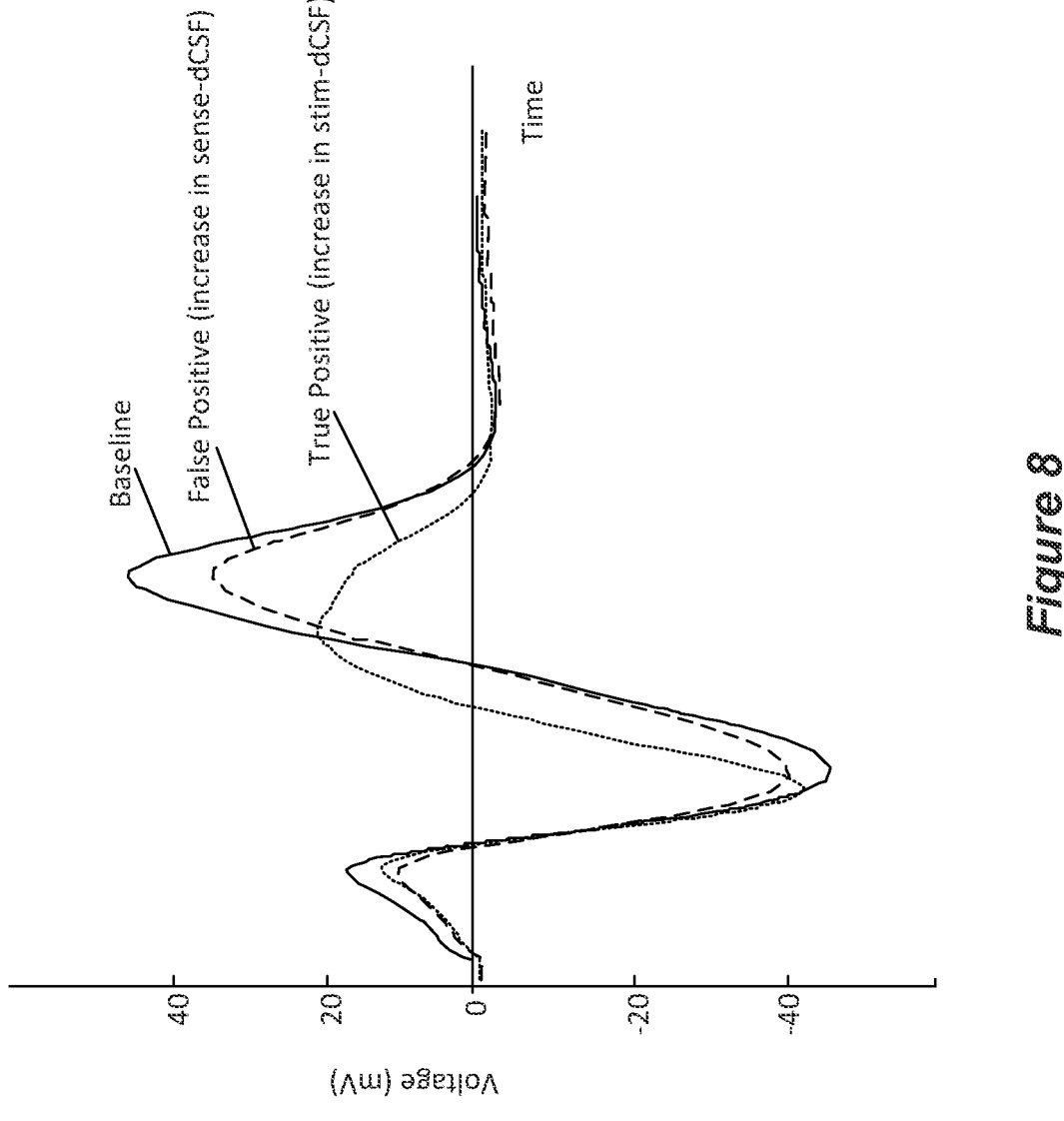
FIG. 8 shows neural responses obtained with differences in stim-dCSF and sense-dCSF.

FIG. 8 illustrates neurological modeling that shows how ECAPs recorded in a true positive (change in stim-dCSF) and a false positive (change in sense-dCSF) may differ from each other. The baseline ECAP curve was recorded when the stimulating electrodes and the recording electrodes were the same distance from the spinal cord (each were 2.5 mm from the spinal cord). The baseline electrode-spinal cord configuration is a situation similar to the configuration illustrated in FIG. 6 A. The true positive ECAP curve was recorded when the stimulating electrodes were moved further from the spinal cord (stim. electrode distance: 3.25 mm; recording electrode distance: 2.5 mm). The true positive electrode-spinal cord configuration is a situation similar to the configurations illustrated in FIGS. 6 B and/or 6 C. The false positive ECAP curve was recorded when the recording electrodes were moved further from the spinal cord (stim. electrode distance: 2.5 mm; recording electrode distance: 3.25 mm). The false positive electrode-spinal cord configuration is a situation similar to the configurations illustrated in FIGS. 7 A and/or 7 B. The ECAP amplitudes for both the true positive (stimulating electrode further from the spinal cord) and the false positive (recording electrode further from the spinal cord) are lower than the base line, as expected. Note, however, that the morphology (i.e., the shape of the curve) of true positive ECAP curve changes compared to the baseline ECAP curve. By contrast, the morphology of the false positive ECAP curve is largely preserved, even though the amplitude of the curve is decreased.

The inventors have realized that the morphology of the recorded neural responses (i.e., the shape of the recorded neural responses) can be used to determine if (or to what extent) a change in the neural response (compared to a baseline neural response) is attributable to a change in the stimulation environment versus a change in the sensing environment. Thus, the decision to (or to what extent to) implement closed-loop feedback can be based on morphological (i.e., shape) changes in the neural response, not simply changes in amplitude. For example, features that are related to the neural response amplitude, such as $N1$-$P2$ amplitude and curve length may be sensitive to both the stimulation environment and the sensing environment. Other examples of amplitude-based features may include the maximum range of the neural response, the rectified area under the curve (AUC), and the curve length, for example. Conversely, features that are more related to the morphology of the neural response signal, such as the N1 time and conduction velocity may be sensitive to changes in the stimulation environment and not as sensitive to changes in the sensing environment. As used herein, the terms morphology and shape are used interchangeably with respect to the recorded neural response and refer to characteristics that are not simply reflective of scaling the amplitude of the recorded neural response signal. Other examples of morphology-based features may include the latency of the various extrema (N1, P2, etc.), the width of the N1-P2 period, the ratio of peaks (e.g., N1 to P2 ratio), the number of extrema, and other line-shape features, such as skew, kurtosis, etc.

Figure 9:
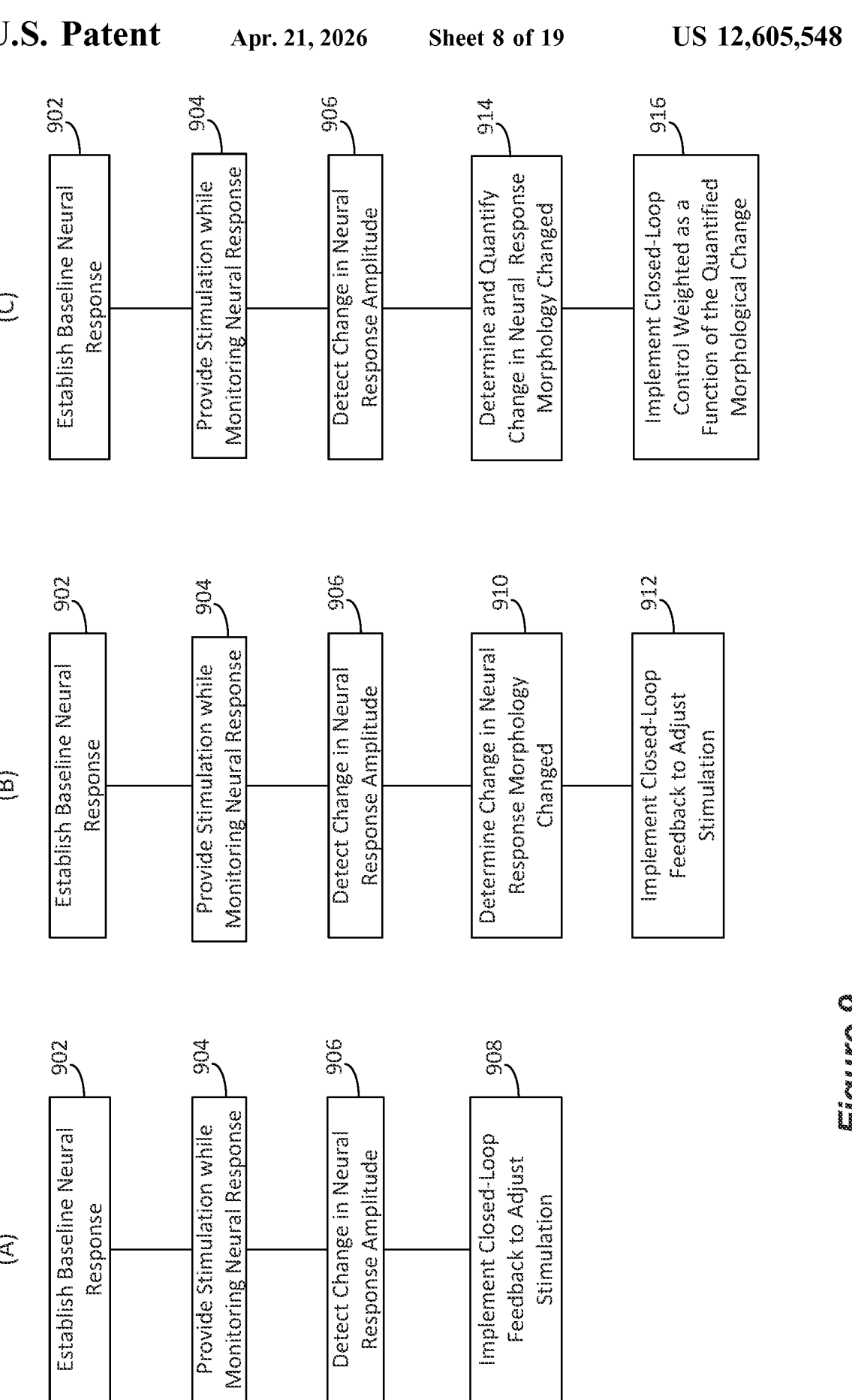
FIG. 9 shows different paradigms for using sensed neural responses for closed-loop feedback.

FIG. 9 illustrates three paradigms for using a sensed and/or recorded neural response for closed-loop feedback for adjusting stimulation parameters. According to paradigm A, at step 902, a baseline neural response (i.e., an initial set point for the recorded neural response features) is established by determining one or more neural response features that correspond to effective therapy for the patient. For example, a fitting procedure, as mentioned above, may be performed on the patient implanted with electrode leads connected to a stimulator device (i.e., either an IPG 100 or an ETS) that comprises stimulation and sensing circuitry configured to operate as described herein. During the fitting procedure, stimulation defined by various stimulation programs is provided to the patient to determine the stimulation parameters that result in the best therapy for the patient (e.g., the best pain relief with the least side effects). Examples of stimulation parameters that may be varied include stimulation amplitude, frequency, pulse width, pulse pattern, and any other parameters known in the art, as well as the location of the stimulation (i.e., which electrodes are used to provide the stimulation and how current is fractionated between the electrodes). For each of the stimulation programs, neural responses are sensed/recorded at one or more sensing electrodes. When the best set of stimulation parameters is identified, the sensed neural response corresponding to that set of stimulation parameters may be recorded and one or more features of the neural response may be determined. The neural response features may be any of the neural response features described above (e.g., amplitude, N1-P2 amplitude, etc.) and one or more of the determined neural response features may be set as the baseline neural response corresponding to the most effective therapy. Typically, neural response features related to amplitude (such as N1-P2 amplitude, curve length, etc.) are selected as the baseline, since it is less computationally intensive to use those features for closed-loop feedback.

At step 904, stimulation is provided to the patient, for example, according to the stimulation parameters determined in step 902. The neural response is also periodically sensed/recorded. At step 906, assume that a change in the neural response compared to the baseline neural response is detected. For example, assume that the amplitude of the sensed neural response has decreased. Upon a change in the sensed neural response, a closed-loop feedback algorithm may be implemented (step 908), which may adjust the stimulation parameters in an attempt to bring the neural response back into agreement with the baseline neural response. For example, if the amplitude of the sensed neural response decreases, the closed-loop feedback algorithm may increase the stimulation amplitude. Examples of suitable closed-loop feedback algorithms are known in the art and described in the references mentioned above. Examples of closed-loop feedback algorithms may use Kalman filtering algorithms, heuristic algorithms, simple threshold model, proportional-integral-derivative (PID) controller models, and the like.

Notice that paradigm A is an example of a naïve methodology, as discussed above, since it assumes that any change in the sensed neural response is due to a change in the stimulation environment and is not due to a change in the sensing environment. For example, if the decrease in the sensed neural response amplitude is due to a change in the sensing environment, then implementing the closed-loop feedback algorithm to increase the stimulation may result in overstimulating the patient.

Paradigm B is one embodiment of an improved methodology of implementing closed-loop feedback based on sensed neural responses, as disclosed herein. The steps of establishing a baseline neural response, providing stimulation while monitoring the neural response, and detecting a change in the neural response amplitude (steps 902, 904, and 906, respectively) may be similar to those steps described with regard to paradigm A. However, in paradigm B, if a change in the neural response amplitude is detected, the algorithm further checks to see if the morphology of the neural response has changed with respect to the baseline neural response (step 910). Methods of determining a morphology change are discussed in more detail below. As described above, changes in the stimulation environment (i.e., situations where adjustment of stimulation is probably warranted), typically result in both amplitude changes and morphology changes in the recorded neural signal. However, changes in the sensing environment (i.e., situation where adjustment of stimulation is not warranted) typically result only in changes to the amplitude of the neural response signal and not changes in the morphology. Thus, in paradigm B, if the change in the amplitude of the neural response signal is accompanied by a change in the neural response morphology, the algorithm implements closed-loop feedback to adjust the stimulation parameters (step 912). However, if the change in the amplitude is not accompanied by a change in morphology, the algorithm does not implement closed-loop feedback, because in that instance, the amplitude change is likely only a result of a change in the sensing environment. Paradigm B is therefore less likely to make unwarranted adjustments to the stimulation parameters.

Paradigm C is another embodiment of an improved methodology of implementing closed-loop feedback based on sensed neural responses, as disclosed herein. Again, the steps of establishing a baseline neural response, providing stimulation while monitoring the neural response, and detecting a change in the neural response amplitude (steps 902, 904, and 906, respectively) may be similar to those steps described with regard to paradigm A. However, in paradigm C, if a change in the neural response amplitude is detected, the algorithm further determines if the morphology of the neural response has changed with respect to the baseline neural response and quantifies the morphology change (step 914). As with paradigm B, if there is no change (or very little change) in the morphology, then the algorithm does not implement closed-loop feedback to adjust the stimulation. However, if there is a morphological change, then the algorithm quantifies the morphological change and implements closed-loop feedback (step 916). The extent of closed-loop feedback is weighted based on the quantification of the morphological change. Methods of determining and quantifying a morphological change and weighting the closed-loop feedback algorithm are described below.

Paradigm C considers that a given change in the recorded neural response amplitude may be due to both a change in the stimulation environment and a change in the sensing environment. For example, if there is a significant change in the neural response amplitude and only a relatively small morphological change, it is likely that the changes are due mostly to a change in the sensing environment with a minor attribution to a change in the stimulation environment. In that case, some adjustment to the stimulation may be warranted, but not as much adjustment as would be suggested based on the amplitude change alone. Thus, the a relatively small weight will be assigned to the closed-loop feedback so that the feedback is not implemented strongly.

Both paradigms B and C involve determining if the morphology of the neural response is changed to determine if (or to what extent) to implement closed-loop feedback for adjusting the stimulation. According to some embodiments, determining a morphological change may comprise determining a change in one or more of the neural response features that are indicative of morphology, such as the N1 time and/or the conduction velocity, as described above. For example, one embodiment of an algorithm may comprise monitoring an amplitude-related neural response feature, such as the N1-P2 amplitude (or the like). If a change in the amplitude-related neural response feature is detected, the algorithm can then calculate a change in a morphology-related neural response feature, such as the N1 time and/or the conduction velocity. If the change in the morphology-related neural response feature exceeds a certain threshold, the algorithm can implement closed-loop feedback using the amplitude-related feature as the feedback variable. As mentioned above, the amount of feedback used (e.g., the gain of the feedback control algorithm) may be weighted as a function of the amount of the change in the morphology-related feature.

According to some embodiments, determining a morphological change may comprise implementing one or more mathematical correlation techniques to determine a morphological change in the recorded neural response, compared to the baseline neural response. Examples of such correlation techniques include cross-correlation, cross-coherence, mutual information, cross-entropy, cross-spectral entropy, and the like. Again, the algorithm may monitor an amplitude-related neural response feature, such as the N1-P2 amplitude (or the like). If a change in the amplitude-related neural response feature is detected for a recorded neural response, then the algorithm may apply one or more of the correlation techniques to determine how the morphology of the recorded neural response correlates to the baseline sensed neural response. The algorithm may determine a correlation coefficient (r) indicating the degree of correlation. For example, assume that a correlation coefficient of 1 indicates perfect correlation. In that case, even though the amplitude of the recorded neural response has changed (with respect to the baseline response), the morphology of recorded neural response has not changed. Thus, closed-loop feedback would not be implemented. Alternatively, the algorithm may perform an autocorrelation on the baseline signal to get a baseline correlation metric, then compare cross-correlations to this autocorrelation. The algorithm may also pre-normalize one or both of the signals to the same x and y axes prior to the auto or cross-correlations to avoid artificially inflating or reducing the correlation metric on the basis of intensity or sampling method differences alone. According to some embodiments, the algorithm may determine a morphology coefficient (M), based on the correlation coefficient, that indicates an extent of morphology change. For example, M may be defined as ($M=1-r$). If the value of M exceeds a predefined threshold value, then the algorithm may implement closed-loop feedback. According to some embodiments, the closed-loop feedback may be weighted as a function of M.

According to some embodiments, changes in morphology may be determined based on comparing one or more waveform features of the recorded neural response with those of the baseline neural response. For example, a difference in the number of extrema (e.g., P1, P2, P3, . . . N1, N2, N3, etc.) may be determined. According to some embodiments, time differences between waveform features may be compared. For example, the time differences between corresponding available extrema may be compared or summed. For example, a sum (S) may be defined as $S=\Delta t_1+\Delta t_2+\Delta t_3+\Delta t_4 \ldots$, where $\Delta t_1$ is the time difference between the P1 peaks (if available), $\Delta t_2$ is the time difference between the N1 peaks, $\Delta t_3$ is the time difference between the P2 peaks, $\Delta t_4$ is the time difference between the N2 peaks (if available), etc. Notice that if the morphology of the recorded neural response does not change significantly compared to the baseline neural response, the value of S will be small, even if the amplitudes of the two neural responses are different. However, if the morphology of the recorded neural response differs significantly from the base baseline neural response, the value of S will be relatively large. Accordingly, according to some embodiments the algorithm may compute a value for S and implement closed-loop adjustment of stimulation if the value of S exceeds a predefined threshold value. According to some embodiments, the algorithm may weight the closed-loop adjustment as a function of S, for example, by adjusting the gain of the closed-loop controller.

Note that the sum S may be considered as analogous to the morphology coefficient M discussed above, in that it provides an indication of a quantified change in the morphology of the neural response signal.

The inventors have also determined that the stimulation artifact (discussed above) is sensitive to changes in the stimulation and sensing electrode environments. Specifically, the artifact may be more sensitive to changes in the sensing environment (sense-dCSF) than to changes in the stimulation environment (stim-dCSF). The stimulation artifact is quasi-static, i.e., it travels at the speed of light and does not exhibit the latency or morphology changes that are associated with neural signal. The amplitude of the stimulation artifact decays at a much faster rate than neural response signals and the artifact's decay is inversely proportional to the conductivity of the tissue medium, which is primarily associated with the location of the sensing electrodes. The source of the stimulation artifact (i.e. its distance from the recording electrode) is a much more known quantity (e.g., the distance from recording electrode is known if recording and stimulating electrodes are on same lead) than the source of the sensed neural response. On this basis, it may also be a more reliable baseline signal. Therefore, distortions to the stimulation artifact may be more indicative of a change in the coupling of the stimulation and sensing electrodes (i.e. whether the sensing electrode may have moved) than, necessarily, a change in coupling between the stimulation electrode and the spinal cord. Accordingly, the stimulation artifact can be used to provide additional information for determining if changes in the ESG are due to changes in the stimulation environment or changes in the sensing environment.

FIG. 10 illustrates a decision matrix illustrating the use of a sensed stimulation artifact and a sensed neural response signal for determining whether (or to what extent) to implement closed loop feedback adjustment of stimulation parameters. In situation A, the distances of both the stimulating electrodes and the sensing electrodes with respect to the spinal cord changes. That situation is expected to cause the most change in the stimulation artifact (i.e., the stimulation artifact amplitude compared to the baseline amplitude determined during calibration). In B, only the distance of the stimulating electrodes changes. This change is similar to the configurations illustrated in FIGS. 6 B and 6 C. Such a change in the distance of the stimulating electrodes will likely cause a change in the stimulation artifact amplitude (compared to baseline), but the amount of change will be smaller than when the distances of both the stimulating and sensing electrodes have changed. In C, the distance of the sensing electrodes changes and the distance of the stimulating electrodes does not change. This change is similar to the configurations illustrated in FIGS. 7 A and 7B. The resulting change in the stimulation artifact will likely be less than in situation A but greater than in situation B, since the stimulation artifact is more sensitive to the recording environment than to the stimulation environment.

According to some embodiments, a threshold may be predefined for a change in the stimulation artifact amplitude. As the stimulation artifact is monitored, if the amplitude changes by an amount AA that exceeds the predefined threshold, that can cause the algorithm to query the neural response signal. Querying the neural response signal may comprise determining a change in the neural response amplitude and a change in the neural response morphology. If the neural response morphology has changed (for example, if it has changed to an extent exceeding a predefined change threshold), then closed-loop feedback may be implemented.

If only the neural response amplitude (and not the morphology) has changed, then the algorithm will not implement closed-loop feedback.

Figure 11:
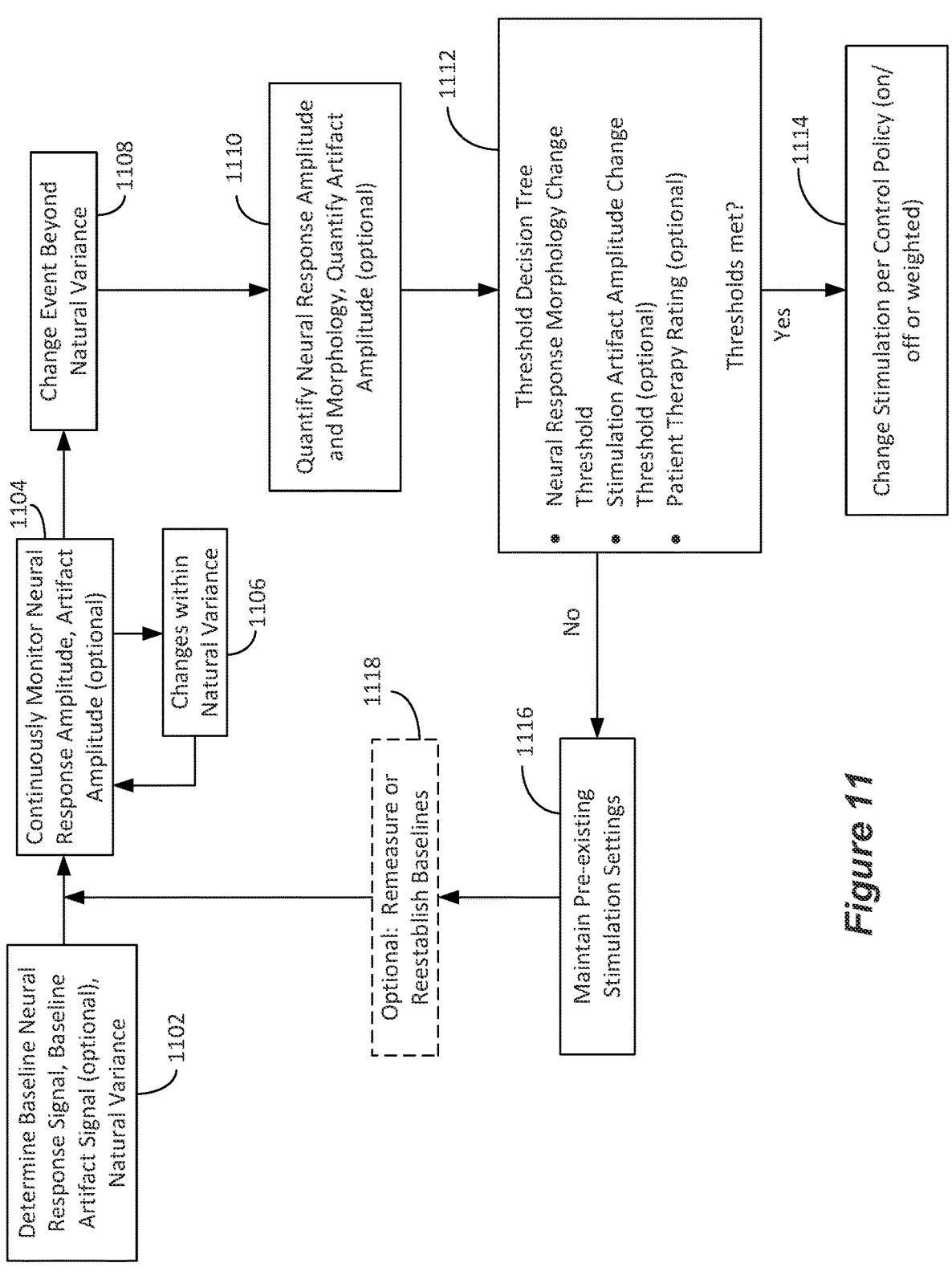
FIG. 11 shows an embodiment of an algorithm for implementing closed-loop feedback control considering neural response morphology.

FIG. 11 illustrates a systems-level implementation of some embodiments of the methods and systems described herein. At step 1102, baseline values for the sensed neural response and stimulation artifact (optional) are determined, for example, during a fitting procedure as described above. The neural responses and artifacts may be recorded with using constant stimulation settings with the patient in a constant posture (e.g., sitting). The natural range of amplitudes of the ESG (i.e., the neural response signals and the stimulation artifact) can be determined. Baseline values and natural variances for the selected amplitude-based and the selected morphology-based features can be determined. With the patient in a constant posture, the stimulation amplitude and/or pulse width can be varied to assess how the morphological features of the neural response changes. With the stimulation at a high setting, the patient can be instructed to change postures and neural response amplitude and morphological feature changes can be noted.

At step 1104 the patient is provided stimulation therapy and the neural response amplitude and the stimulation artifact amplitude (optional) is continuously monitored. If any changes in the amplitude values are within the natural variances (step 1106) determined during the calibration, then no action is taken, and stimulation therapy is continued using the pre-existing stimulation settings. If a change in the amplitude values outside the natural variance is detected (step 1108), then the selected morphology-related features and optionally the artifact amplitude are quantified, as described above (step 1110). Changes in the morphology-related features (and optionally, the artifact amplitude) are compared to threshold values determined during the calibration phase (or set by the system), to determine if closed-loop feedback should be implemented to adjust the stimulation settings (step 1112). It should be mentioned here that patient feedback, such as patient therapy ratings, may also inform the decision to implement closed-loop feedback. For example, the patient may be given an option to periodically rate their therapy using their external controller. If the patient does not indicate a change regarding their therapy, then the algorithm may decide not to implement closed-loop feedback. If the changes in the morphology-related features meet the threshold criteria for adjusting stimulation, then closed-loop feedback can be implemented (step 1114). As mentioned above, and described in more detail below, the closed-loop feedback gain may be weighted based on the magnitude of the changes in the morphology-related features to account for the attribution of stimulation environment changes versus sensing environment changes on the neural response amplitude. If the changes in the morphology-related features do not meet the threshold criteria for adjusting stimulation, then the pre-existing stimulation settings can be maintained for providing stimulation (step 1116). According to some embodiments, the patient may be provided an opportunity to remeasure and/or reestablish the baseline feature values, for example, by implementing a calibration routine on their external controller (step 1118).

Referring again to steps 1108-1112, when a sensed neural response amplitude is encountered that is outside the natural variance with respect to the baseline neural response amplitude, the algorithm must decide if (or to what extent) to implement closed-loop control. According to some embodiments, the algorithm determines if changes in one or more selected morphology-based features exceed a predetermined threshold value. If the answer is no, then the algorithm assumes that the change in the sensed neural response amplitude is due to changes in the sensing environment and does not implement closed-loop control. If the answer is yes, then the algorithm implements closed-loop control to adjust one or more of the stimulation parameters to reduce the error between the baseline neural response amplitude (i.e., the set point) and the measured neural response amplitude (i.e., the control variable or feedback variable).

Closed-loop feedback control is well known in the art and is not discussed here in detail, but the control scheme may involve controllers such PID controllers, Kalman filters, or the like. For the purposes of this discussion, assume that the closed-loop feedback control scheme uses a proportionality constant ($K_p$) to determine the adjustment of a stimulation parameter (y). The stimulation parameter may be the stimulation amplitude, pulse width, frequency, etc., or some combination of such parameters. The value of the constant $K_p$ dictates how strongly the adjustment is applied. Applying the control scheme, the present value of the manipulated variable $y_i$ will be the previous value of the manipulated variable (i.e., parameter) $y_{i-1}$ adjusted by $K_p$, for example, $y_i=y_{i-1}+K_p$. But according to some embodiments, this control scheme will only be applied if the changes morphology-based features exceed the predefined threshold value.

According to other embodiments, the closed-loop feedback control scheme can be weighted based on the changes in the morphology-based features. For example, the morphology-based features (and possibly the amplitude based features) can be used to calculate a weighting factor (w), that modulates how strongly the feedback adjustment is applied. According to these embodiments, the present value of the manipulated variable may be determined as $y_i=y_{i-1}+wK_p$, or $y_i=w(y_{i-1}+K_p)$, as examples. Generally, w should be directly correlated with features that point to morphological changes and inversely correlated with changes that reflect natural variability or amplitude-only changes. For example, the weighting factor w may be based on the morphology coefficient M or sum S, calculated as described above. According to some embodiments, the weighting factor w may be expressed as a ratio of feature values, wherein the features that are indicative of a morphological change are included in the numerator and features that are indicative of amplitude-only are included in the denominator. Alternatively, the weighting factor w may be expressed as a sum/difference, wherein the morphological factors are additive, and the amplitude-only features are subtractive. Moreover, the features may be normalized to account for their sensitivity, so that factors that are highly sensitive do not overwhelm the others.

Figure 12:
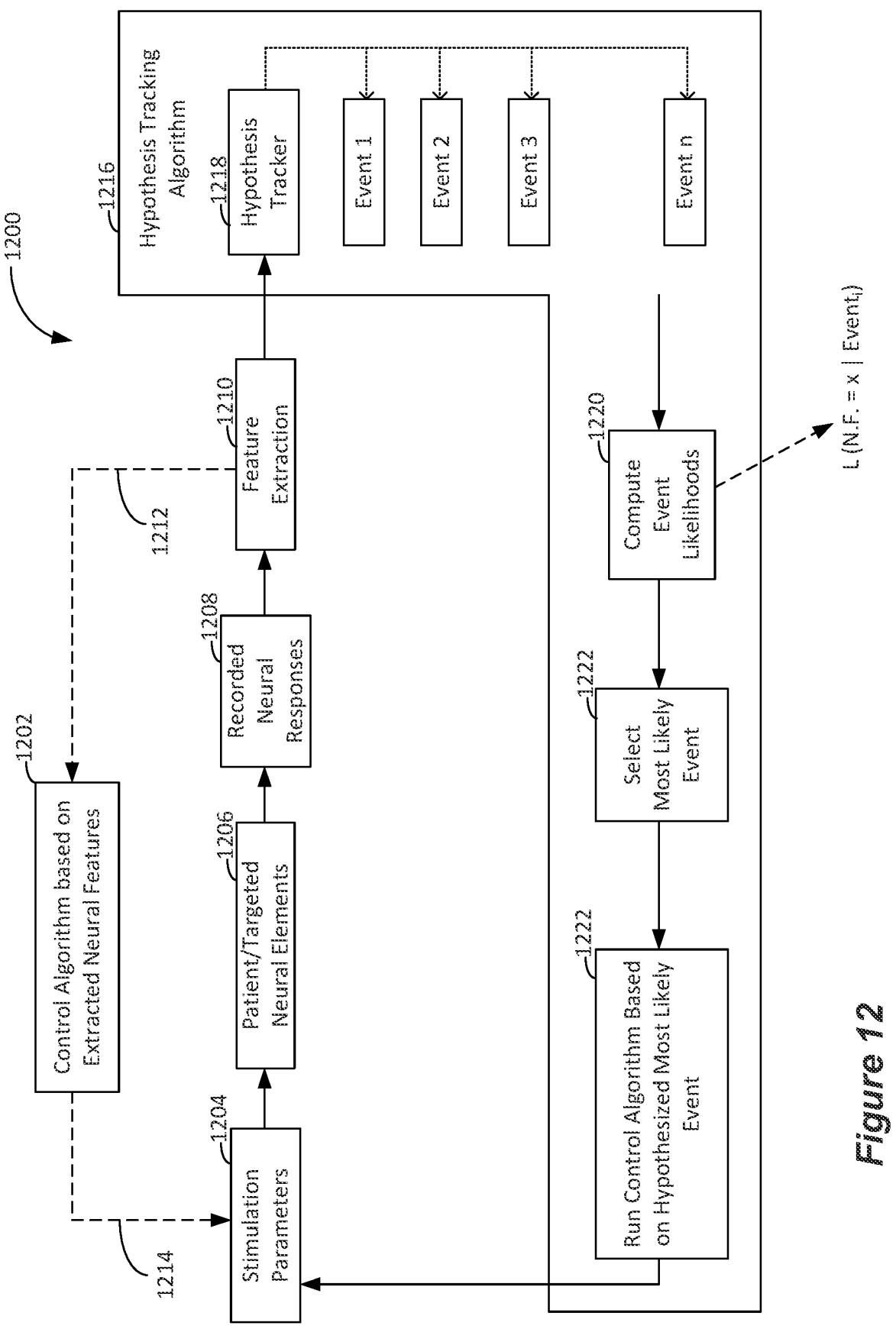
FIG. 12 shows an embodiment of an algorithm for implementing closed-loop feedback control including a hypothesis tracking algorithm.

FIG. 12 illustrates an overview of another embodiment for an improved control system using closed-loop feedback control to adjust stimulation parameters based on sensed neural responses. Assume that the control system 1200 includes a control algorithm 1202 for adjusting stimulation parameters based on neural features extracted from recorded neural signals. As mentioned above, the control algorithm 1202 may be any feed-back algorithm, such as Kalman filtering algorithms, heuristic algorithms, simple threshold model, proportional-integral-derivative (PID) controller models, and the like. The control algorithm 1202 may be used to control one or more stimulation parameters 1204, such as current amplitude, frequency, pulse width, stimulation fractionalization, and the like. The stimulation modulates one or more neural elements of the patient 1206 and evoked neural responses are recorded 1208. Features of the recorded neural responses can be extracted 1210, as described above. The extracted feature(s) may be fed into the control algorithm (line 1212), which may adjust the stimulation parameter(s) (line 1214) based on the extracted feature(s).

According to some embodiments, the control algorithm 1202 uses probabilistic modeling of features and dynamical systems modeling to adjust stimulation parameters to compensate for changes in dorsal width of cerebrospinal fluid (dCSF) as the electrode(s) move with respect to the spinal cord, for example, in response to postural changes. The mathematical modeling may include using one or more of a Kalman filter or a Hidden Markov Model (HMM), in various embodiments. As is known in the art, the algorithm may be provided with training data by performing a training data procedure whereby stimulation is provided to the patient and sensed electrical activity is recorded to determine a relationship between the sensed electrical activity and neurostimulation. The training procedure may involve applying stimulation to the patient as they assume different postures, perform various movements, and the like, and may involve varying stimulation parameters. Once the relationships are determined, the neurostimulation may be modulated according to the determined relationship.

Notice that the feedback control described thus far with respect to FIG. 12 is potentially naïve, in that it assumes that changes in the extracted features are due to changes in the stimulation environment, and therefore implicate adjustment to the stimulation parameters. (That is why the lines 1212 and 1214 are shown as dashed lines). But, as described above, changes in the extracted features may be, at least in part, caused by changes in the sensing environment, and thus, change to stimulation parameters may not be warranted. Moreover, the relationships determined for the underlying probabilistic modeling of features and dynamical systems modeling used for the control algorithm may not be able, at this point, to discriminate between events that implicate the sensing environment (sense-dCSF) and events that implicate the stimulation environment (stim-dCSF).

Accordingly, an improvement of the control system 1200 resides in the hypothesis tracking algorithm 1216. The hypothesis tracking algorithm 1216 comprises a hypothesis tracker 1218, which receives the extracted neural feature of the neural response as input. Embodiments of a hypothesis tracker are described in more detail below. At a high level, the hypothesis tracker algorithmically hypothesizes an array of possible events that could have happened to cause the observed extracted neural feature. Examples of possible events in the array include events such as the stimulating electrode(s) moving further from the spinal cord, the stimulating electrode(s) moving closer to the spinal cord, the sensing electrode(s) moving further from the spinal cord, the sensing electrode(s) moving closer to the spinal cord, combinations of these, etc. The hypothesis tracking algorithm 1216 is configured to compute likelihoods 1220 for each of the events in the array. In other words, for a measured neural feature (N.F.) value of x, the hypothesis tracking algorithm computes a likelihood (L) of a given event (Event). This results in an array of likelihoods, corresponding to the array of events in the hypothesis tracker 1218. The hypothesis tracker 1218 keeps track of each of the event possibilities over time. Once the likelihoods are calculated, the event with the highest likelihood is selected 1222. The control algorithm is run based on the most likely hypothesized event 1224. For example, if the most likely event is that the distance between the stimulating electrode(s) and the spinal cord has increased, then the stimulation amplitude may be increased. Conversely, if the most likely event is that the distance between the sensing electrode(s) has increased and the stimulating electrode(s) distance has not changed, then the stimulation amplitude may remain constant. Also, as described in more detail below, as the hypothesis tracking algorithm runs, certain events may be determined to be more likely than other events. The hypothesis tracking algorithm may update the underlying probabilistic modeling of features and dynamical systems modeling used for the control algorithm to account for those changing likelihoods.

Figure 13:
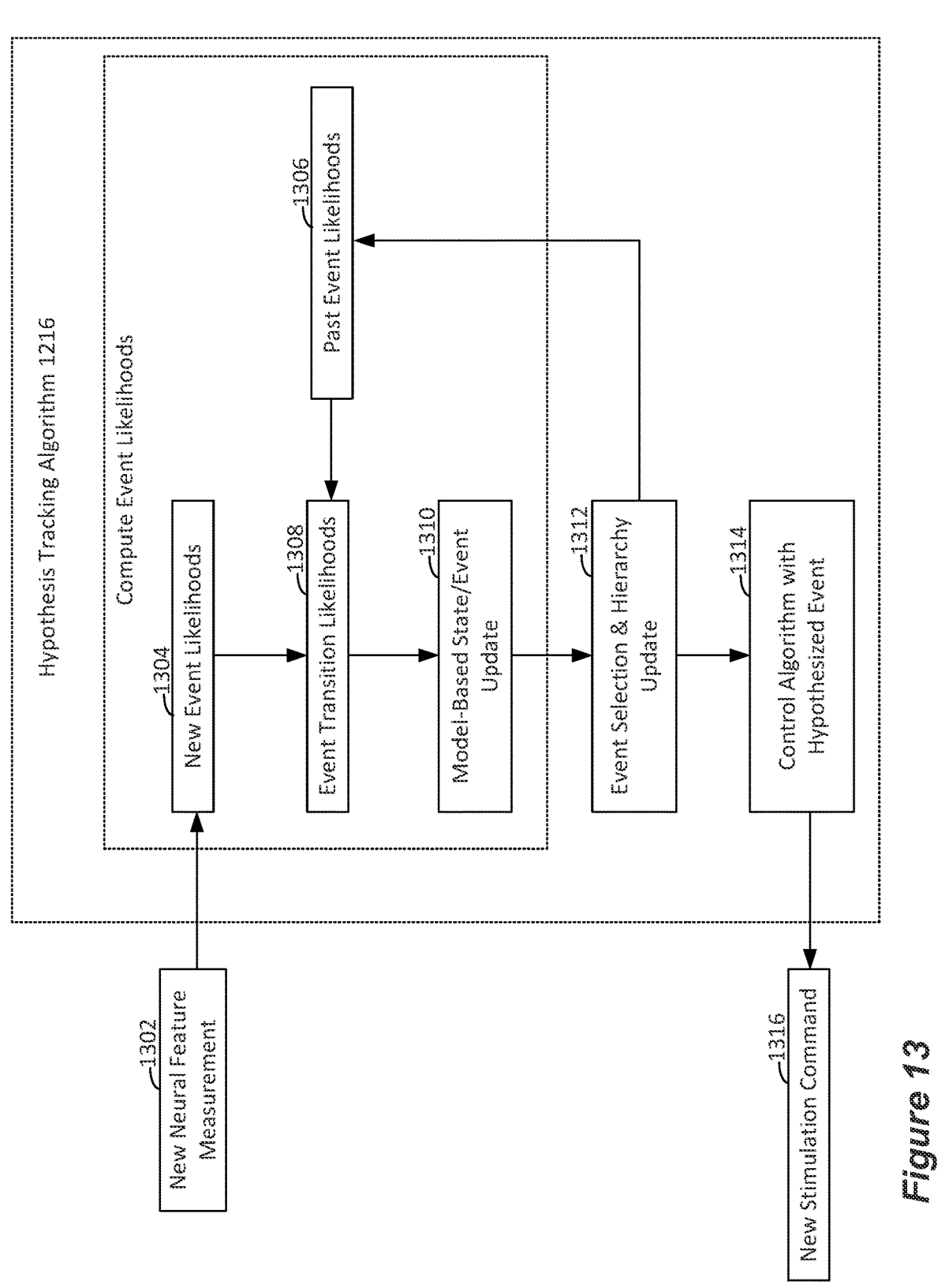
FIG. 13 shows an embodiment of an algorithm for implementing closed-loop feedback control including a hypothesis tracking algorithm.
Figure 14:
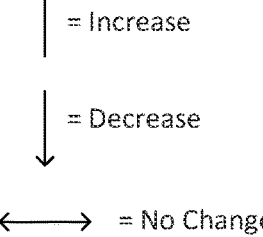
FIG. 14 shows an embodiment of a table of event likelihoods for various changes in neural features.

FIG. 13 illustrates further aspects of the hypothesis tracking algorithm 1216. A new neural feature measurement 1302 is fed to the hypothesis tracking algorithm. At step 1304, the hypothesis tracking algorithm evaluates likelihoods for events that might have caused the instant neural feature measurement. Different possible events have different inherent likelihoods based on the physics and/or kinematics of the system. FIG. 14 illustrates an embodiment of how event likelihoods can be evaluated. FIG. 14 illustrates a table 1400. The table 1400 may be embodied as a look-up table, for example. The first column 1402 lists an extracted neural feature measurement, which is fed into the hypothesis tracking algorithm. In the illustrated embodiment, the extracted neural feature is an amplitude change, for example, N1-P2 amplitude, or other amplitude-related feature of the neural response. An increase in the amplitude is represented as an up-arrow, a decrease is represented by a down-arrow, and no change is represented by a horizontal arrow. Generally, any one or more neural features may be included in the table. The second column 1404 enumerates various events (i.e., Event). Thirteen events are included in the table 1400 for the purposes of illustration. The third column 1406 shows the behavior at the sensing electrode for the given event, expressed as a change in the amount of CSF between the electrode(s) and the spinal cord (dCSF). A decrease in dCSF (down-arrow) indicates that the electrode is closer to the spinal cord; and increase in dCSF (up-arrow) indicates that the electrode is further from the spinal cord. The fourth column 1408 shows the behavior at the stimulating electrode(s). The fifth column 1410 indicates the likelihood for the particular event, ranked from high to very low. Note that numerical values may be used to rank the likelihoods, for example, on a scale of 0 to 1, with 0 being very unlikely and 1 being very likely, but words are used in the table for illustration purposes. The sixth column 1412 indicates the change to stimulation amplitude that would be appropriate, given the occurrence of the particular event. For example, if the dCSF at the stimulating electrode decreases, the appropriate therapy adjustment would be to decrease the stimulation amplitude.

Still referring to FIG. 14, notice that events 1-5 are all associated with a measured increase in the neural response amplitude. Event 1 is that both the sensing electrode(s) and the stimulating electrode(s) moved closer to the spinal cord. Event 1 is highly likely to be associated with an increase in the neural response amplitude. Event 2 is that the sensing electrode(s) moved closer to the spinal cord and the stimulating electrode(s) stayed the same distance from the spinal cord. Event 2 is assigned a likelihood of medium, because Event 2 could be responsible for the increase in neural response amplitude, but it is generally predicted that both the sensing and stimulating electrodes will move in concert with each other, so Event 2 is less likely than Event 1. Event 3 is that the sensing electrode(s) moved very much closer to the spinal cord (the great extent of the move is indicated by double down-arrows) while the stimulating electrode(s) moved away from the spinal cord. Event 3 would also result in an increase in the measured neural response amplitude, but it is very unlikely that the two sets of electrodes would move in such opposite directions. Accordingly, Event 3 is assigned a very low likelihood. Given this description of Events 1-3, the remainder of the events listed in table 1400 and their assigned likelihoods should be apparent.

Referring again to FIG. 13, once likelihoods have been assigned to events that may be responsible for the new neural feature measurement (i.e., step 1304, for example, based on likelihoods in Table 1400 (FIG. 14)), those likelihoods are combined with past determined event likelihoods to determine an event transition likelihood (step 1308). Event transition likelihoods may also be preconfigured or initially preloaded. The event transition likelihood determination can be thought of as the probability that a given event is responsible for the observed neural response measurement, based on (1) the likelihood that the event would occur (e.g., as described in table 1400, FIG. 14), and (2) the state of the system immediately prior to measuring the new neural feature. The state of the system immediately prior to measuring the new neural feature is important because it may be assumed that the system is not likely to change abruptly in a very short period of time. In other words, some amount of "smoothness" may be assumed. This is because of the timescale of the measurements, which may be on the order of milliseconds or hundreds of milliseconds. For example, if at time t, the sensing electrode(s) and/or the stimulating electrode(s) are moving away from the spinal cord, it is unlikely that the electrodes will be suddenly moving toward the spinal cord at time t+1 (unless an accompanying biomarker change signifies this possibility (e.g. sensed neural response also becomes much larger)). In other words, the likelihood that a given event is responsible for an observed neural response measurement may be based on the event likelihoods reflected in the lookup table 1400 (FIG. 14) adjusted by highest likelihood events determined for previous measurements.

Figure 15:
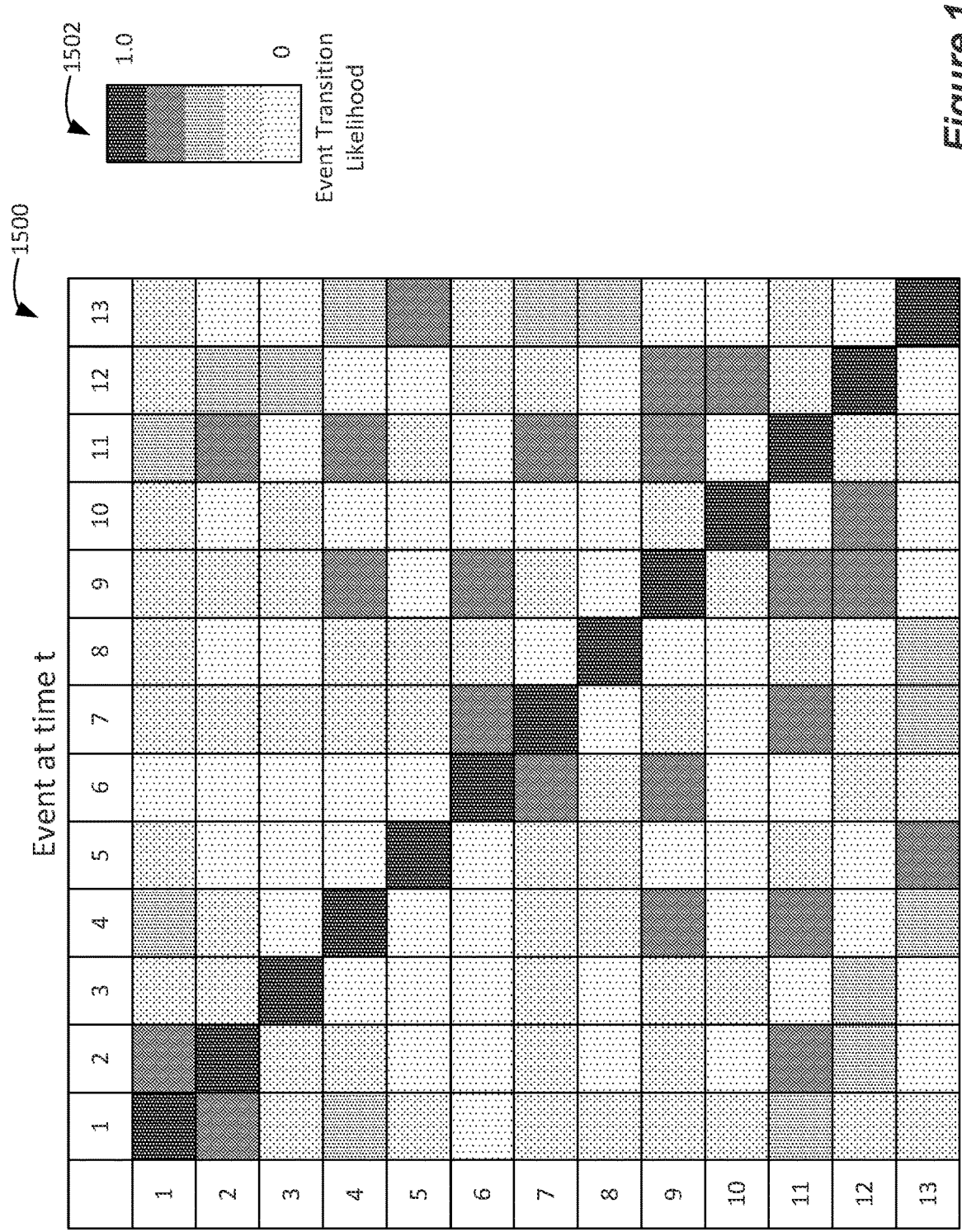
FIG. 15 shows an embodiment of a table of event transition likelihoods.

FIG. 15 illustrates a table 1500 of event transition likelihoods for the events 1-13 shown in table 1400 (FIG. 14). The top row lists events occurring at time t (e.g., the previous event) and the left column lists events at time t+1 (e.g., the current predicted event). The intersections of the grid denote the likelihood that a transition from one event to another would occur. The likelihoods may be denoted numerically, for example, on a scale from 0 to 1, with 0 being very unlikely and 1 being very likely. The table 1500 illustrates these likelihoods using a color map, as illustrated in the scale 1502. Factors used to calculate the transition likelihoods are discussed in more detail below. But for a qualitative understanding of table 1500, consider the first column of Table 1500 where the event at time t is Event 1 (i.e., both the sense-dCSF and the stim-dCSF is decreasing (See Table 1400, FIG. 14)). Event 1 involves both the distance between both sensing electrode(s) and the stimulating electrode(s) and the spinal cord decreasing. If Event 1 is occurring at time t, it is likely that Event 1 will also be occurring at time t+1. Accordingly, the intersection of times t and t+1 have a probability close to 1. Conversely, if Event 1 is occurring at time t, it is unlikely that Event 6 (i.e., both sense-dCSF and stim-dCSF increasing) will be occurring at time t+1. Accordingly, the intersection of times t and t+1 for a transition from Event 1 to Event 6 has a low probability. The fact that some event transitions are unlikely effectively reduces the space (dimensionality reduction) for the overall event probabilities, as discussed in more detail below.

Figure 16:
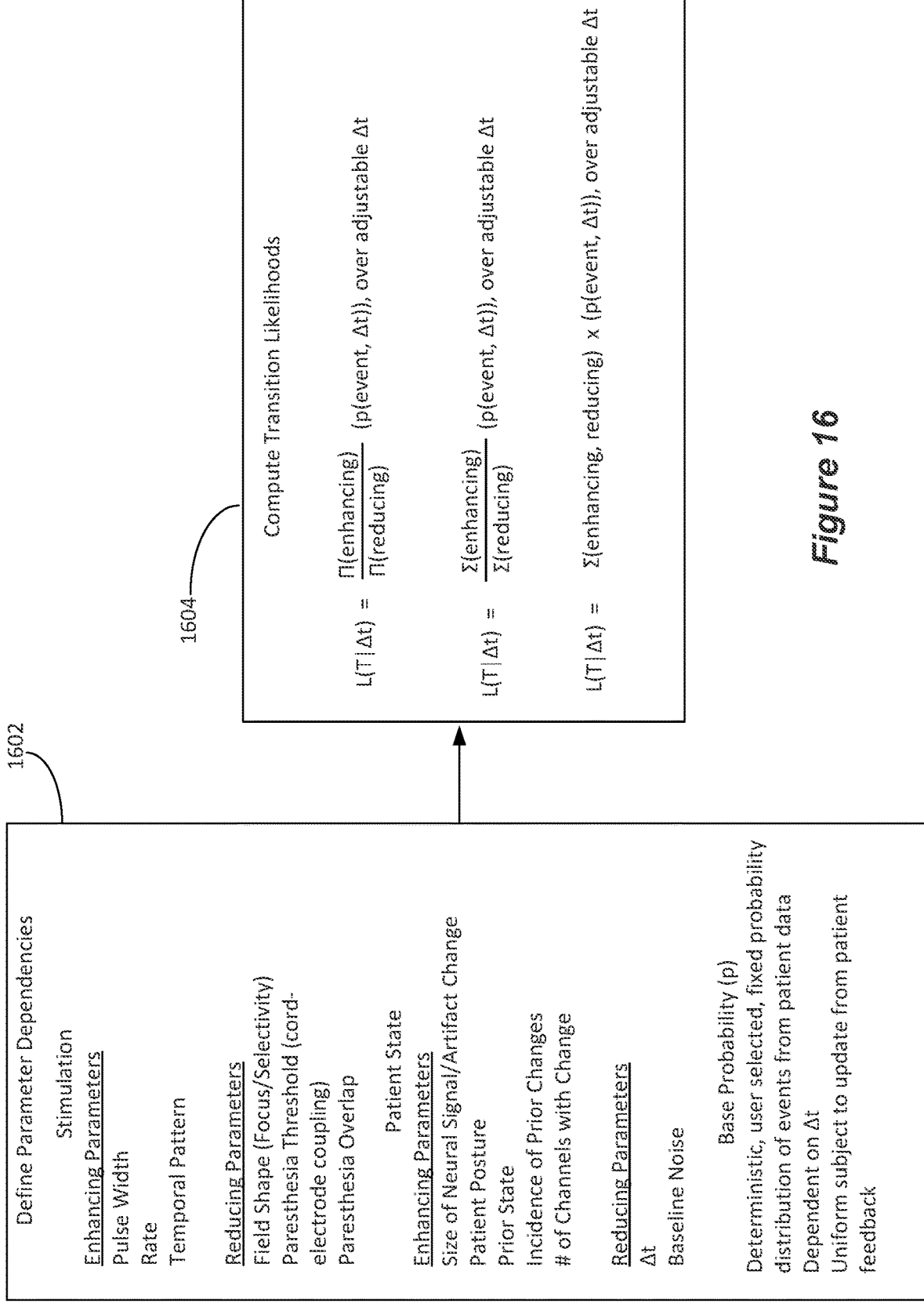
FIG. 16 shows an embodiment of factors for calculating event transition likelihoods.

FIG. 16 illustrates example algorithms for determining event/transition likelihoods. The likelihoods of event transitions may depend on a number of different parameters, some of which enhance the likelihood that an event transition will occur and others of which reduce the likelihood. In FIG. 16, the block 1602 lists some examples of such dependency parameters. The dependency parameters may be hard-coded into the algorithm or they may be selectable, for example, using a graphical user interface (GUI). In the illustrated embodiment, the parameters are divided into parameters related to the stimulation, the patient state, and general base probabilities for transitions occurring. Examples of stimulation-related dependency parameters include pulse width, stimulation rate, and temporal pattern. Increasing these parameters may enhance the likelihood of event transitions. Likewise, stimulation parameters may include aspects such as field shape, paresthesia threshold, and paresthesia overlap, which generally relate to the degree of coupling between the stimulation and the targeted neural elements and are typically inversely related (i.e., reducing) to the probability of event transitions. In other words, if the stimulation is more robustly coupled to the targeted neural elements, slight changes in electrode/spinal cord configuration may be less likely to result in significant changes to the therapeutic efficacy. Patient state dependency parameters may include enhancing factors, such as the sizes of the neural signal and/or artifacts, patient posture, the prior patient state, and the incidences of prior event changes. Reducing parameters may include the refresh rate $\Delta t$ (i.e., noise is likely to be more of a factor with long $\Delta t$) and other baseline noise factors. Other transition dependency factors may be base probabilities, which may be intrinsic probabilities for particular events happening. For example, transitions from one event state to a radically different event state in a short time period is inherently low and will have a low base probability. Other factors may contribute to the base probability, for example, clinical studies or data collected from other patients indicating that certain events are more or less likely to happen. The base probabilities may be user selected, and/or may have fixed probability distributions. Note that more or fewer dependency factors than those illustrated may be used in the transition likelihood determination.

Weights may be associated with the various enhancing and reducing dependency factors. According to some embodiments, the various dependency factors may be selected using a GUI, for example, by using dropdown menus, and the weights assigned for each dependency parameter may be selected, for example, using a sliding bar or knob of the GUI. Once weights are assigned to the various dependency factors, the transition likelihoods may be calculated based on the weights. Box 1604 of FIG. 16 illustrates three methods of calculating a likelihood L that an event transition T in a time $\Delta t$. According to some embodiments, the likelihood may be calculated as a product of the weights for the enhancing factors divided by the weights for the reducing factors, with the result being multiplied by the base probability for the event. According to some embodiments, the likelihood may be calculated as the sum of the enhancing factors divided by the sum of the reducing factors, with the result being multiplied by the base probability for the event. According to some embodiments, the likelihood may be calculated as the sum of the enhancing and reducing factors (with the reducing factors given negative weights), with the result being multiplied by the base probability for the event. According to some embodiments, the probability tables may be adjusted iteratively, for example, using feedback.

Figure 17:
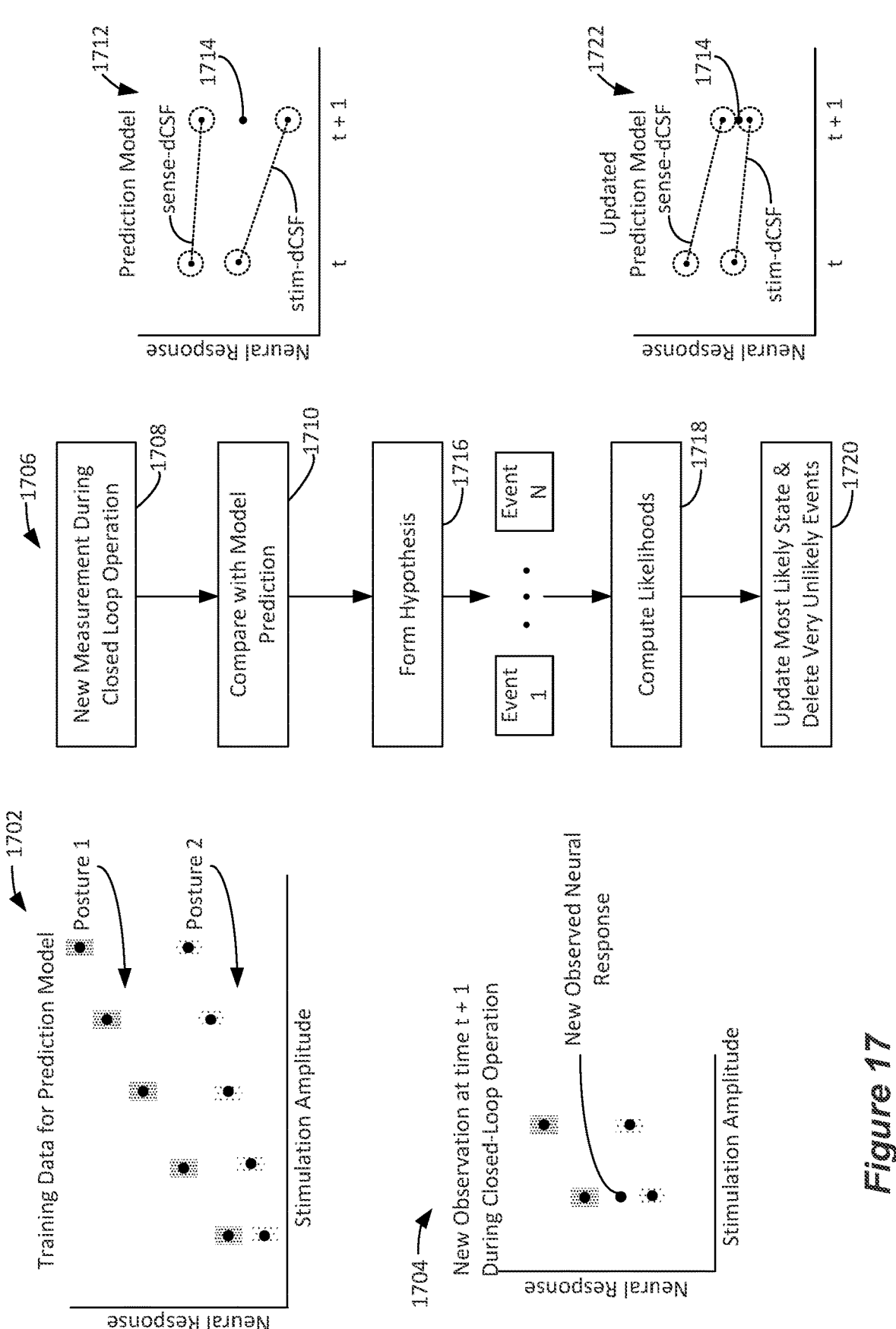
FIG. 17 shows an embodiment of an algorithm for updating a base prediction model using computed event transition likelihoods.

Referring again to FIG. 13, once the event transition likelihoods are calculated (step 1308) based on the new observed measurement and likelihood combined with the past event likelihood, the event transition likelihood may be used to update and/or refine the prediction model used for the control algorithm (step 1310). FIG. 17 illustrates an embodiment of updating/refining the prediction model. As mentioned above, some embodiments of the control algorithms described herein use mathematical modeling including using one or more of a Kalman filter or a Hidden Markov Model (HMM) to model relationships between the sensed neural signals and the state of the spinal cord vis-à-vis the stimulating and sensing electrodes. In particular, the models may predict the sense-dCSF and/or stim-dCSF with respect to the sensed neural signals. With such control algorithms, the control decision may be thought of a direct mapping from an estimated state of the model. Assume that the prediction model has been trained with data, such as illustrated in graph 1702. The training protocol involves stimulating the patient according to a range of stimulation parameters and measuring the neural response observed with each set of stimulation parameters. In the illustration, the stimulation amplitude was varied, but any one or more stimulation parameters may be varied, as described above. Graph 1702 shows training data collected with two different patient postures. The shaded clouds surrounding each of the data points denote error associated with the measurements.

Graph 1704 illustrates a neural response measured at a time (t+1) during the operation of the closed loop algorithm. Four data points from the training data (and associated error clouds) are shown on the graph 1704 for reference. Notice that the new neural response measurement lies outside of the trends established using the training data. The workflow 1706 illustrates an embodiment of how the disclosed algorithms may work on the new observed neural response using the hypothesis tracking algorithm described above to update the prediction model in view of the new observed neural response. At step 1708, the new measurement is provided to the control algorithm. At step 1710, the control algorithm compares the new observed neural response to the prediction model. As shown in graph 1712, the prediction model is configured to model the neural response behavior (e.g., amplitude) as a function of the stim-dCSF and the sense-dCSF. Each of the predicted neural responses for the sensing and stimulating dCSF values are associated with a cloud representing variance parameters for the predicted values, represented by the dashed circles surrounding the points. Notice that in graph 1712, the measured new neural response 1714 is outside of the variance clouds for both the sense and stim dCSF. Thus, the model is ambiguous as to what event may have caused the new measured neural response value, i.e., and may not be able to determine accurately how to adjust stimulation based on the new value.

At step 1716, the hypothesis tracking algorithm forms hypotheses about the events that may have caused the new measured neural response. At step 1718, the algorithm computes the likelihoods for the hypothesized events. As explained above, based on intrinsic likelihoods and on likelihoods determined for past iterations (e.g., t−1, t, etc.), certain events will be determined to be likely and other events will be very unlikely. At step 1720, the algorithm updates the prediction model with the most likely estimated states and deletes the unlikely states from the underlying prediction model. This acts to refine the prediction model, as illustrated in the graph 1722. Notice that in the updated prediction model, the new observed neural response is within the variance cloud for the predicted stim-dCSF. Thus, the control algorithm can determine a control decision to accurately adjust stimulation based on the new observed neural response. With each iteration of the control algorithm the base prediction model can be updated based on the algorithm at each timestep.

Referring again to FIG. 13, once the state of the prediction model is updated (step 1310) based on the calculated most (and least) likely events, the likelihoods for the most likely event can be selected (step 1312) for the purpose of informing the control algorithm. The calculated event likelihoods can also be saved for informing the next iteration (as per step 1306). At step 1314, the control algorithm is run using the selected most likely event, which may control the stimulator to issue a new stimulation command (step 1316) using the stimulation parameters adjusted according to the control algorithm.

The embodiment illustrated in FIG. 13, and specifically the step of adjusting the base prediction model (step 1310) presupposes that the control algorithm is a technique that involves a base prediction model such as a Kalman filter. However, according to some embodiments, model-free control algorithms, such as PID controllers, may be used. With such a control algorithm, control decision is based on error between the measured neural feature and a set point. The algorithm may adjust the stimulation according to a pre-defined gain (i.e., how strongly feedback is applied) to minimize the error between the measured neural feature and the set point. According to some embodiments, the hypothesis tracking algorithms described herein can be used to modulate the gain and/or the set point of the control algorithm based on the determined most likely events (determined for example, as described with respect to FIGS. 14-16).

Figure 18:
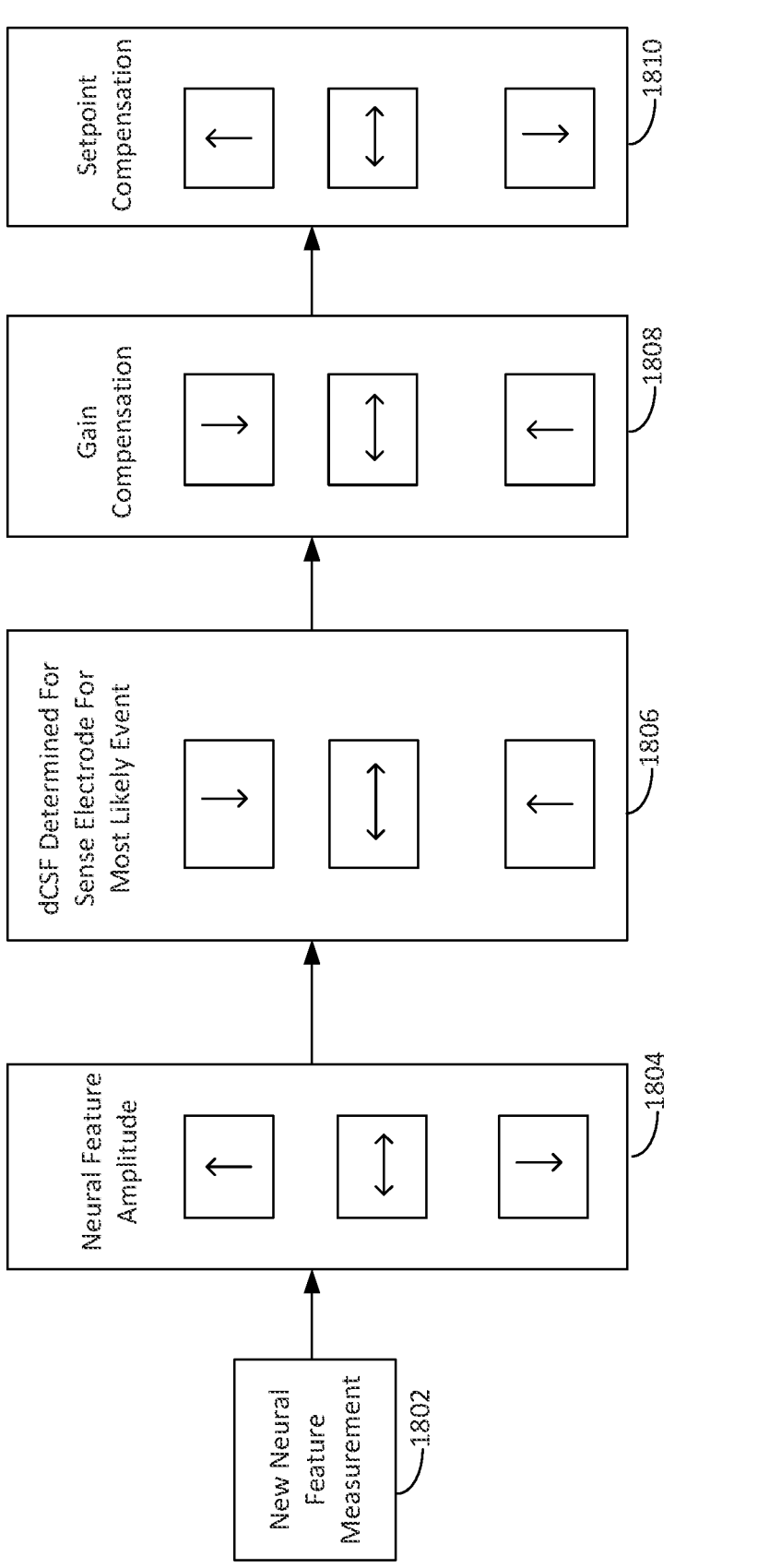
FIG. 18 shows an algorithm for adjusting gain scheduling and/or setpoints of a model-free control algorithm using computed event transition likelihoods.

FIG. 18 illustrates an example of adjusting a model-free control algorithm based on hypothesis tracking. At step 1802, assume a new neural feature measurement is obtained. In the illustrated example, the neural feature is an amplitude-based feature, for example, N1-P2 amplitude. It could be any of the neural features described above. At step 1804, the algorithm determines if the neural feature has increased (up-arrow), stayed the same (horizontal arrow), or decreased (down arrow). At step 1806, the algorithm computes the likelihoods of events that could have caused the new measured neural response using techniques such as those described above with respect to FIGS. 14-16. The algorithm determines the most likely event. In the illustrated embodiment, the most likely event is determined with respect to the behavior of the sensing electrode(s), i.e., whether the sensing electrode moved closer to the spinal cord (dCSF-sense decreased), stayed the same distance from the spinal cord (no change in dCSF-sense), or moved away from the spinal cord (dCSF-sense increased). At step 1808, the algorithm may adjust the gain used by the control algorithm (known in the art as "gain scheduling"). At step 1810, the algorithm may adjust the setpoint used by the control algorithm.

In the illustrated example of the embodiment, the top row of possibilities involve an increase in the neural signal amplitude. Assume that the hypothesis tracking algorithm determined that the most likely event involves the sensing electrode(s) moving closer to the spinal cord (decrease in dCSF-sense). In that case, the algorithm may decrease the gain of the control algorithm to avoid overstimulating the patient. Likewise, the algorithm may increase the setpoint of the control algorithm. If the most likely event involves no change in the sense-dCSF, then the algorithm may leave the gain and setpoint of the control algorithm unchanged. If the most likely event involves an increase in the sense-dCSF, then the algorithm may increase the gain and decrease the setpoint of the control algorithm.

Figures 19, 20:
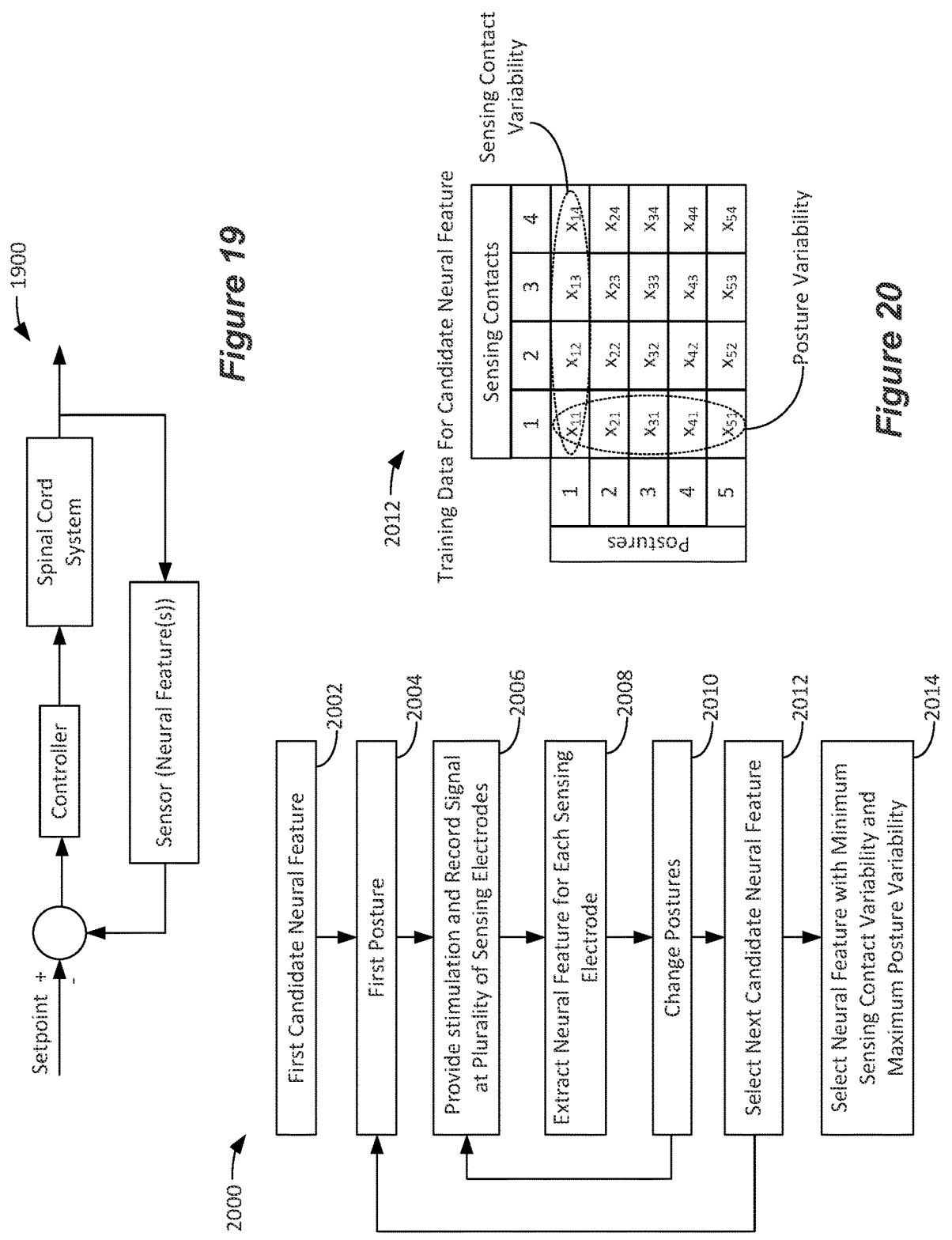
FIG. 19 shows an embodiment of a simplified control algorithm.
FIG. 20 shows an embodiment of an algorithm for selecting extracted neural features for closed-loop control.

As will be apparent from the above discussion, aspects of the disclosure involve closed-loop feedback control of stimulation parameters using one or more sensed neural features as a control variable. FIG. 19 illustrates a simplified control diagram 1900, whereby a controller (e.g., an IPG) controls stimulation based on the sensed neural feature(s). As explained above, ideally the sensed neural response feature(s) (i.e., neural features) used for feedback are maximally sensitive to the stimulation environment and minimally sensitive to the sensing environment. Appreciate that the neural response features that are sensitive to the stimulation environment only and the features that are sensitive to both the stimulation and the sensing environment may be patient specific. Accordingly, according to some embodiments, testing may be performed with a patient to determine which features are best suited for implementing closed-loop feedback. For example, a patient implanted with an electrode lead may undergo a testing procedure, whereby stimulation parameters (amplitude, pulse width, frequency, etc.) and/or the center point of stimulation (i.e., which electrodes are used to provide the stimulation) are varied. The impact of changes in stimulation geometry and/or the stimulation waveform can thereby be tied to changes in the neural response features to determine which neural response features are most sensitive to stimulation for that patient. Such testing may be performed while the patient remains very still in a constant posture (e.g., sitting, lying down, etc.) and while the patient moves through a series of postures.

FIG. 20 illustrates an embodiment for selecting a neural feature for closed-loop feedback. The illustrated workflow 2000 is based on two assumptions. The first assumption is that different sensing electrodes are different distances from the spinal cord, and thus have differing amounts of intervening dCSF (i.e., sense-dCSF). The second assumption is that when stimulation is applied at the same stimulating electrode(s) when the patient is in different postures, the spinal cord—contact distance may change causing a difference in intervening dCSF (i.e., stim-dCSF). At step 2002, a candidate neural feature to potentially be used for closed-loop feedback is selected. The candidate neural feature (i.e., neural response feature) may be any of the neural features described above. At step 2004, the patient is positioned in a first posture. At step 2006, stimulation is provided at a given stimulating electrode and electrical activity is recorded at a plurality of sensing electrodes (i.e., sensing contacts). At step 2008, the candidate neural feature is extracted from the recordings at each of the sensing electrodes. At step 2010, the patient changes postures and the process of stimulating, sensing, and extracting the neural features for each of the sensing contacts is repeated for the new posture. The process may be repeated for several different patient postures.

Table 2012 illustrates training data collected for a candidate neural feature. The table comprises the extracted neural feature value $x_{ij}$ collected for the candidate neural feature at each of the plurality of sensing contacts for each of the different patient postures. A metric R can be determined for data in table 2012. R is the normalized variability of each of the row-vectors, which corresponds to the normalized variability with respect to the sensing contact. Also, a metric C can be determined for the data in table 2012. C is the normalized variability of each of the column-vectors, which corresponds to the normalized variability with respect to patient posture. The goal is to select a neural feature that has a high normalized variability with respect to posture and a low normalized variability with respect to the sensing contact. According to some embodiments, a function J may be defined, for example J=R/C, or J=aC+bR (where a and b are coefficients), for the candidate neural feature.

Referring again to the workflow 2000, at step 2012 a next candidate neural feature is selected, and the process is repeated (thereby generating a table 2012 for the next candidate neural feature). At step 2014, the candidate neural feature with the minimum sensing contact variability and maximum postural variability is selected to use for closed-loop feedback. For example, the candidate neural feature with the minimal J-function (as defined above) may be selected and the closed-loop feedback control algorithm may be run based on that selected neural feature.

Methods for selecting a neural response feature for closed-loop feedback, such as the workflow 2000 described above, may be performed during a patient fitting procedure, as described earlier. Such methods may be performed on, or facilitated by, one or more external devices, such as a clinician's programmer 50 (FIG. 4). According to some embodiments, such an external device may provide a GUI to direct the clinician through the workflow and may be configured with algorithms for determining the variabilities and parameters described above. The external device may further be configured to transmit the determined best one or more neural response features to the patient's stimulator device.

According to some embodiments of the disclosure, sensed neural signals may be processed using one or more processing techniques to yield a processed neural signal to serve as a basis for closed-loop feedback. Examples of processing techniques include frequency domain analysis (such as Fourier transform (FT), fast Fourier transform (FFT), and Hilbert transforms), neural network processing, decomposition techniques, and the like. Ideally, the processed neural signal is variant with respect to stimulation environment (i.e., stim-dCSF) but invariant with respect to sensing environment (i.e., sense-dCSF).

Figure 21:
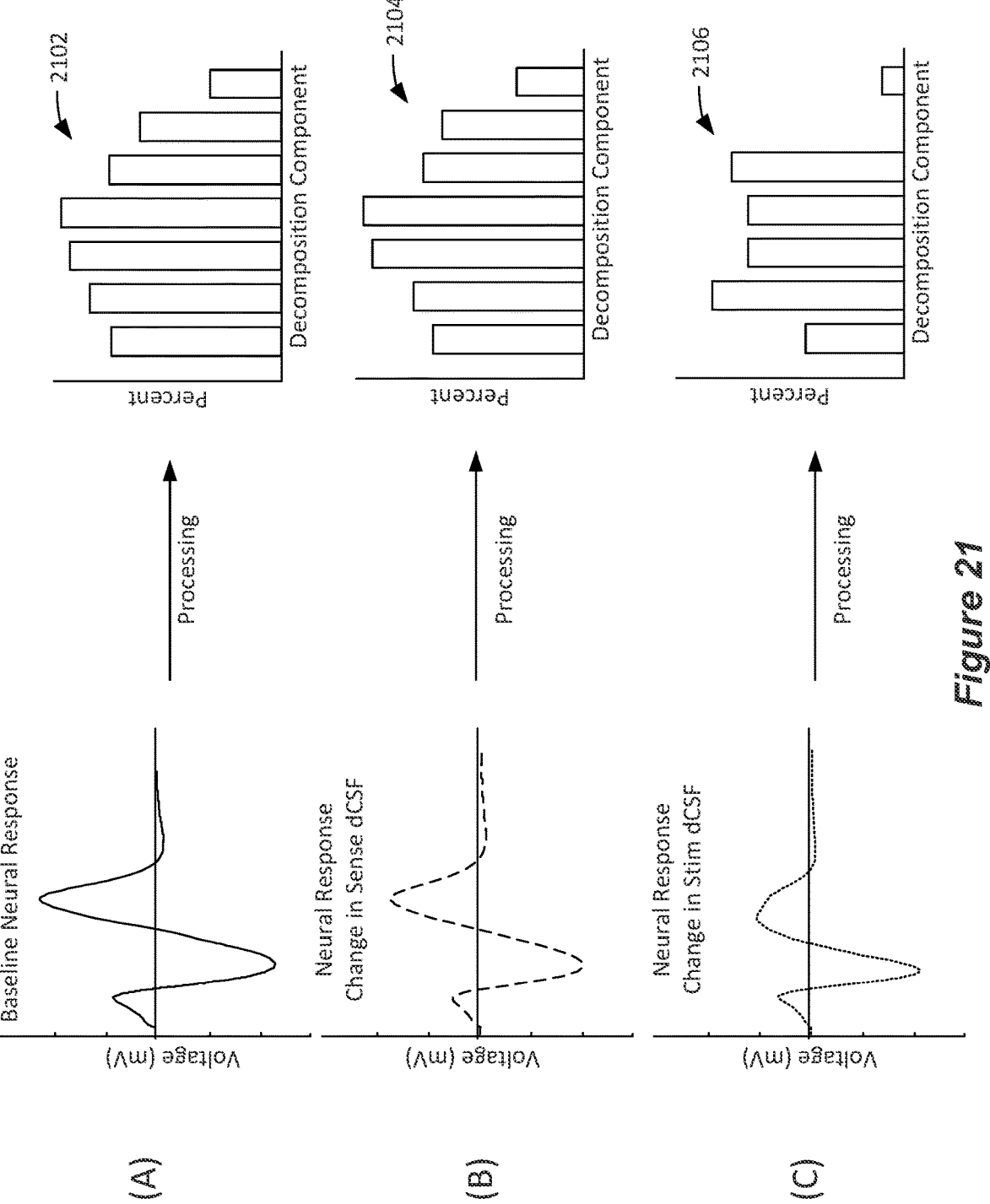
FIG. 21 shows an embodiment of processing a neural response.

FIG. 21 illustrates an embodiment of processing a sensed neural signal to yield a processed neural signal that is invariant with respect to sense-dCSF but variant with respect to stim-dCSF. FIG. 21A shows the baseline recorded neural signal, which is processed to yield a histogram of decomposition components 2102. For example, if the processing involves frequency domain analysis, the decomposition components may comprise frequencies contained within the neural signal. Alternatively, the decomposition components may comprise fiber diameters that are recruited by the stimulation. Alternatively, the decomposition components may comprise conduction velocities of the neural elements recruited by the stimulation. FIG. 21B shows a recorded neural signal when the sense-dCSF has changed, specifically, when the sensing electrode(s) have moved further from the spinal cord. Notice that the amplitude of the neural response is decreased. However, when the neural response is processed as described above, the histogram of the decomposition components 2104 is very similar to the baseline histogram 2102. That is because the components of the sensed neural signal is not expected to change significantly due to a difference in sense-dCSF, even though the amplitude may have changed. In other words, if the stimulating electrodes have not moved, then the same neural elements are expected to be recruited by the stimulation and the decomposition components of the neural response will not change significantly. FIG. 21C shows a recorded neural response when the stim-dCSF has changed, specifically, when the stimulating electrode(s) have moved further from the spinal cord. Notice that the morphology, as well as the amplitude, of the sensed neural response signal has changed.

Moreover, when the neural response signal is processed as described above, the histogram of the decomposition components 2106 is significantly different than the baseline histogram 2102. When the distance between the stimulating electrode(s) and the spinal cord change, different populations of neural elements are recruited, resulting in differences in decomposition components, such as neural fiber sizes, conduction velocities, component frequencies, and the like. The closed-loop algorithm may use such changes in the processed sensed neural signals (e.g., the illustrated histograms) as a basis for implementing closed-loop feedback. For instance, a closed-loop algorithm may attempt to minimize the percentage of small fibers recruited by stimulation or maximize the percentage of large fibers by stimulation, as uncovered by the decomposition components. Similarly, a closed-loop algorithm may attempt to minimize recruitment of slower conducting fibers and maximize recruitment of faster conducting fibers. A salient feature for control may also be the ratio between large vs. small fibers or similarly fast vs. slow fibers.

Although particular embodiments of the present invention have been shown and described, the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A method of providing automatic closed-loop feedback control of stimulation to a patient's spinal cord using an implantable pulse generator (IPG) that is implantable within the patient, wherein the IPG is configured to connect to one or more electrode leads implanted within a spinal column of the patient, the one or more electrode leads comprising a plurality of electrodes, wherein the method is executable by control circuitry of the IPG, the method comprising the following steps:

(i) using one or more of the plurality of electrodes as stimulating electrodes to provide stimulation to neural tissue in the patient's spinal cord, (ii) using one or more of the plurality of electrodes as sensing electrodes to sense neural responses evoked in the neural tissue by the stimulation, (iii) determining a first value for a first feature of the sensed neural responses, wherein the first feature is indicative of an amplitude of the sensed neural responses, (iv) upon detection of a change in the first value, determining a second value for a second feature of the sensed neural responses, wherein the second feature is indicative of a shape of the sensed neural responses, and (v) if both the first value and the second value have changed, the second value change being a change with respect to a baseline value for the second feature, adjusting the stimulation based on one or more of the first value and the second value, otherwise not adjusting the stimulation and returning to step (i).

2. The method of claim 1, wherein the at least one second feature is more sensitive to changes in an environment between the stimulating electrodes and the neural tissue than to changes in an environment between the sensing electrodes and the neural tissue.

3. The method of claim 2, wherein the changes in an environment between the stimulating electrodes and the neural tissue comprise changes in a thickness of cerebrospinal fluid (dCSF) between the stimulating electrodes and the neural tissue.

4. The method of claim 1, wherein the first feature comprises one or more of an amplitude of any peak of the sensed neural responses, and area under a curve, a curve length, and a difference between amplitudes of any two peaks of the sensed neural responses.

5. The method of claim 1, wherein the second feature comprises one or more of a duration of a portion of the sensed neural responses, a conduction velocity, a latency of a feature of the sensed neural responses, a number of extrema, skew, and kurtosis.

6. The method of claim 1, further comprising determining a difference between the second value and the baseline value and adjusting the stimulation only if the difference exceeds a threshold.

7. The method of claim 1, wherein adjusting the stimulation comprises using a feedback control algorithm to adjust the stimulation.

8. The method of claim 7, wherein the feedback control algorithm adjusts the stimulation to maintain the first value with respect to a set point for the first value.

9. The method of claim 7, wherein the feedback control algorithm comprises a Kalman filter.

10. The method of claim 7, wherein the feedback control algorithm comprises a proportional-integral-derivative (PID) control model.

11. The method of claim 7, wherein the feedback algorithm comprises a gain and wherein the gain is adjusted based on the second value.

12. The method of claim 1, wherein adjusting the stimulation comprises adjusting one or more parameters of the stimulation selected from the group consisting of stimulation amplitude, frequency, pulse width, pulse pattern, and center point of stimulation.

13. A medical device comprising:

an implantable pulse generator (IPG) implantable in a patient and configured to connect to a plurality of electrode nodes, each electrode node configured to be coupled to an electrode that is implantable in a spinal column of the patient and configured to contact spinal cord tissue of the patient;

wherein the IPG comprises control circuitry configured to:

use one or more of the plurality of electrodes as stimulating electrodes to provide stimulation to neural tissue in the patient's spinal cord, use one or more of the plurality of electrodes as sensing electrodes to sense neural responses evoked by the stimulation, determine a first value for a first feature of the sensed neural responses, wherein the first feature is indicative of an amplitude of the sensed neural responses, upon detection of a change in the first value, determine a second value for a second feature of the sensed neural responses, wherein the second feature is indicative of a shape of the sensed neural responses, and if both the first value and the second value have changed, the second value change being a change with respect to a baseline value for the second feature, adjust the stimulation based on one or more of the first value and the second value, otherwise not adjust the stimulation.

14. The medical device of claim 13, wherein the at least one second feature is more sensitive to changes in an environment between the stimulating electrodes and the neural tissue than to changes in an environment between the sensing electrodes and the neural tissue.

15. The medical device of claim 14, wherein the changes in an environment between the stimulating electrodes and the neural tissue comprise changes in a thickness of cerebrospinal fluid (dCSF) between the stimulating electrodes and the neural tissue.

16. The medical device of claim 13, wherein the first feature comprises one or more of an amplitude of any peak of the sensed neural responses, and area under a curve, a curve length, and a difference between amplitudes of any two peaks of the sensed neural responses.

17. The medical device of claim 13, wherein the second feature comprises one or more of a duration of a portion of the sensed neural responses, a conduction velocity, a latency of a feature of the sensed neural responses, a number of extrema, skew, and kurtosis.

18. The medical device of claim 13, further comprising determining a difference between the second value and the baseline value and adjusting the stimulation only if the difference exceeds a threshold.

* * * * *